US008999525B2

(12) United States Patent
Lee et al.

(10) Patent No.: US 8,999,525 B2
(45) **Date of Patent: *Apr. 7, 2015**

(54) CONDENSED-CYCLIC COMPOUND, ORGANIC LIGHT-EMITTING DEVICE COMPRISING THE SAME, AND FLAT PANEL DISPLAY APPARATUS INCLUDING THE DEVICE

(75) Inventors: Jae-Yong Lee, Yongin (KR); Seung-Gak Yang, Yongin (KR); Hee-Yeon Kim, Yongin (KR); Jeoung-In Yi, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 534 days.

This patent is subject to a terminal disclaimer.

(21) Appl. No.: 13/333,674

(22) Filed: Dec. 21, 2011

(65) Prior Publication Data

US 2012/0286249 A1 Nov. 15, 2012

(30) Foreign Application Priority Data

May 13, 2011 (KR) ........................ 10-2011-0045118

(51) Int. Cl.
*H01L 51/54* (2006.01)
*C07D 403/10* (2006.01)
(Continued)

(52) U.S. Cl.
CPC ............ *C07D 251/24* (2013.01); *C07D 401/14* (2013.01); *C07D 401/04* (2013.01);
(Continued)

(58) Field of Classification Search
CPC .. C07D 401/14; C07D 401/04; C07D 235/14; C07D 251/24; C07D 487/04; C07D 519/00; C07D 471/04; H01L 51/5056; H01L 51/0055; H01L 51/0067
See application file for complete search history.

(56) References Cited

U.S. PATENT DOCUMENTS 5,281,489 A * 1/1994 Mori et al. .................... 428/690
5,645,948 A 7/1997 Shi et al.
(Continued)

FOREIGN PATENT DOCUMENTS

JP 11-345686 A 12/1999
KR 10-2008-0016007 A 2/2008
(Continued)

OTHER PUBLICATIONS

Translation for WIPO 2010150988 (publication date Dec. 2010).*
(Continued)

*Primary Examiner* — Dawn L. Garrett
(74) *Attorney, Agent, or Firm* — Christie, Parker & Hale, LLP

(57) ABSTRACT

A condensed-cyclic compound is represented by Formula 1 below. An organic light-emitting device includes the condensed-cyclic compound. A flat panel display apparatus includes the organic light-emitting device.

Formula 1

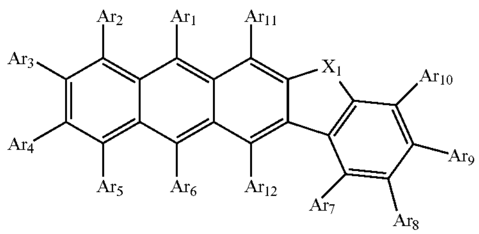

The organic light-emitting device includes an organic layer including the compound of Formula 1 and has low driving voltage, high emission efficiency, and a long lifetime.

20 Claims, 1 Drawing Sheet

(51) Int. Cl.

| | |
|---|---|
| ***C07D 251/24*** | (2006.01) |
| ***C07D 401/14*** | (2006.01) |
| ***C07D 401/04*** | (2006.01) |
| ***C07D 235/14*** | (2006.01) |
| ***C07D 471/04*** | (2006.01) |
| ***C07D 487/04*** | (2006.01) |
| ***C07D 519/00*** | (2006.01) |
| *H01L 51/00* | (2006.01) |
| *H01L 51/50* | (2006.01) |

(52) U.S. Cl.
CPC ............ *C07D235/14* (2013.01); *C07D 471/04* (2013.01); *C07D 487/04* (2013.01); *C07D 519/00* (2013.01); *H01L 51/0055* (2013.01); *H01L 51/0067* (2013.01); *H01L 51/5056* (2013.01); *Y10S 428/917* (2013.01)

(56) References Cited

U.S. PATENT DOCUMENTS

| | | | | |
|---|---|---|---|---|
| 6,171,715 | B1 | 1/2001 | Sato et al. | |
| 6,559,256 | B2 | 5/2003 | Holmes et al. | |
| 2006/0154105 | A1 | 7/2006 | Yamamoto et al. | |
| 2008/0224129 | A1* | 9/2008 | Choi et al. | 257/40 |
| 2008/0226945 | A1 | 9/2008 | Kim et al. | |
| 2011/0057182 | A1 | 3/2011 | Lee et al. | |
| 2012/0161615 | A1* | 6/2012 | Hong et al. | 313/504 |
| 2012/0181520 | A1 | 7/2012 | Kim et al. | |
| 2012/0187392 | A1 | 7/2012 | Ito et al. | |
| 2012/0286246 | A1* | 11/2012 | Kim et al. | 257/40 |
| 2013/0207048 | A1 | 8/2013 | Schwaiger et al. | |

FOREIGN PATENT DOCUMENTS

| | | | | |
|---|---|---|---|---|
| KR | 10-2008-0018573 | A | | 2/2008 |
| KR | 10-0852118 | B1 | | 8/2008 |
| KR | 10-2009-0118859 | A | | 11/2009 |
| KR | 10-2010-0027950 | A | | 3/2010 |
| KR | 10-2011-079401 | A | * | 7/2011 |
| WO | WO 2010/150988 | A2 | * | 12/2010 |

OTHER PUBLICATIONS

Translation for Publication No. KR 10-2011-0079401 (publication date Jul. 2011).*

U.S. Office action dated Apr. 9, 2014, for cross reference U.S. Appl. No. 13/243,817, (17 pages).

* cited by examiner

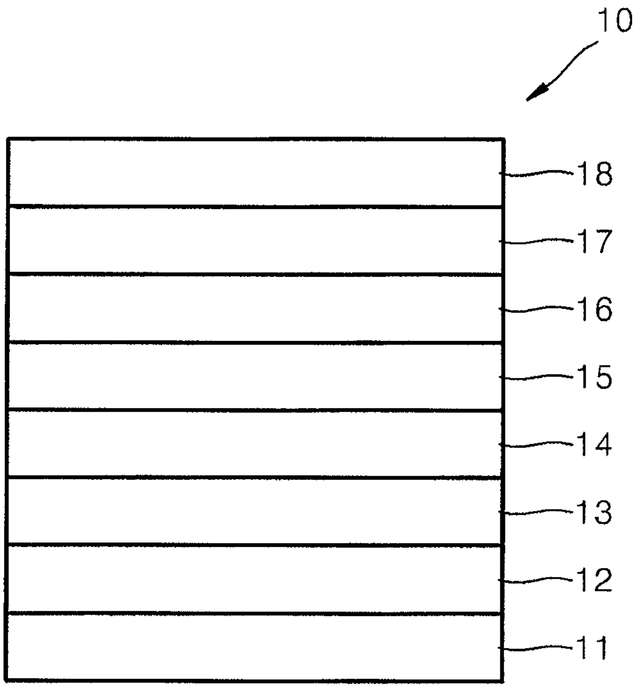
10
18
17
16
15
14
13
12
11

CONDENSED-CYCLIC COMPOUND, ORGANIC LIGHT-EMITTING DEVICE COMPRISING THE SAME, AND FLAT PANEL DISPLAY APPARATUS INCLUDING THE DEVICE

CROSS-REFERENCE TO RELATED PATENT APPLICATION

This application claims priority to and the benefit of Korean Patent Application No. 10-2011-0045118, filed on May 13, 2011 in the Korean Intellectual Property Office, the entire content of which is incorporated herein by reference.

BACKGROUND

1. Technical Field

The present invention relates to a condensed-cyclic compound, an organic light-emitting device including the same, and a flat panel display apparatus including the organic light-emitting device.

2. Description of Related Art

Organic light-emitting devices are self light-emitting devices which have wide viewing angles, good contrast, rapid response times, good brightness, driving voltage, and response speeds, and are multicolored.

In general, an organic light-emitting device includes an anode formed on a substrate, and a hole transport layer, an emission layer, an electron transport layer, and a cathode are sequentially formed on the anode. Each of the hole transport layer, the emission layer, and the electron transport layer is an organic thin-film layer including an organic compound.

The driving method of the organic light-emitting device is as follows. When voltage is applied between the anode and the cathode, holes injected from the anode move to the emission layer through the hole transport layer, and electrons injected from the cathode move to the emission layer through the electron transport layer. Carriers, such as holes and electrons, are recombined in the emission layer and produce excitons. The excitons are changed from an excitation state to a ground state, thereby generating light.

A need still exists for organic light-emitting devices with improved driving voltage, light-emitting efficiency, and lifetime.

SUMMARY OF THE INVENTION

Embodiments of the present invention provide a condensed-cyclic compound, an organic light-emitting device including the condensed-cyclic compound, and a flat panel display apparatus including the organic light-emitting device.

According to embodiments of the present invention, a condensed-cyclic compound is represented by Formula 1 below:

Formula 1

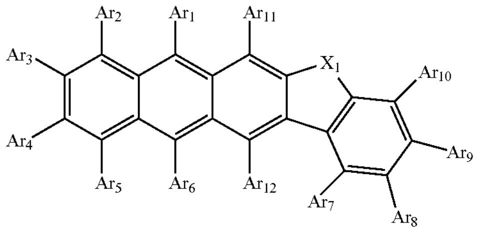

In Formula 1, $X_1$ may be $CR_1R_2$, $NR_3$, O, or S. Each of $Ar_1$ through $Ar_{12}$ is independently selected from hydrogen atoms, deuterium, halogen atoms, hydroxyl groups, cyano groups, nitro groups, carboxyl groups, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, substituted or unsubstituted $C_2$-$C_{30}$ heterocyclic groups, groups represented by Formula 2 below, groups represented by $N(Q_1)(Q_2)$, and groups represented by $Si(Q_3)(Q_4)(Q_5)$. Each of $Q_1$ through $Q_5$ is independently selected from hydrogen atoms, deuterium, halogen atoms, hydroxyl groups, cyano groups, amino groups, nitro groups, carboxyl groups, substituted or unsubstituted $C_1$-$C_{30}$alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, and substituted or unsubstituted $C_2$-$C_{30}$ heterocyclic groups. In some embodiments, at least one of $Ar_1$ through $Ar_{12}$ is a group represented by Formula 2 below;

Formula 2

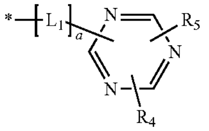

In Formula 2, $L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group. Also, a is an integer from 0 to, and each of $R_1$ through $R_5$ is independently selected from hydrogen atoms, deuterium, halogen atoms, hydroxyl groups, cyano groups, amino groups, nitro groups, carboxyl groups, substituted or unsubstituted $C_1$-$C_{30}$alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, and substituted or unsubstituted $C_2$-$C_{30}$ heterocyclic groups. Plural numbers in $R_4$ and $R_5$ are optionally the same as each other or different from each other.

According to other embodiments of the present invention, an organic light-emitting device includes: a first electrode; a second electrode facing the first electrode; and an organic light-emitting device including at least one organic layer between the first electrode and the second electrode, where the at least one organic layer is formed of the condensed-cyclic compound described above.

According to still other embodiments of the present invention, a flat panel display apparatus includes a transistor including a source electrode, a drain electrode, a gate, and an active layer, and the organic light-emitting device described above, where the first electrode of the organic light-emitting device is electrically connected to the source electrode or the drain electrode.

BRIEF DESCRIPTION OF THE DRAWINGS

The above and other features and advantages of the present invention will become more apparent by reference to the following detailed description when considered in conjunction with the attached drawings in which:

FIG. 1 is a schematic cross-sectional view of an organic light-emitting device according to an embodiment of the present invention.

DETAILED DESCRIPTION OF THE INVENTION

According to embodiments of the present invention, a condensed-cyclic compound is represented by Formula 1 below:

Formula 1

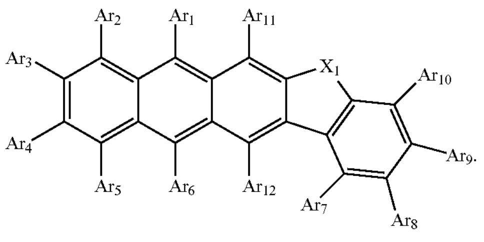

In Formula 1, $X_1$ is $CR_1R_2$, $NR_3$, O, or S. Each of $Ar_1$ through $Ar_{12}$ is independently selected from hydrogen atoms, deuterium, halogen atoms, hydroxyl groups, cyano groups, nitro groups, carboxyl groups, substituted or unsubstituted $C_{10}$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, substituted or unsubstituted $C_2$-$C_{30}$ heterocyclic groups, groups represented by Formula 2 below, groups represented by $N(Q_1)(Q_2)$, and groups represented by $Si(Q_3)(Q_4)(Q_5)$.

Formula 2

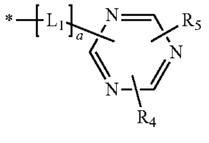

In Formula 2, $L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group. Also, a is an integer from 0 to 5, and each of $R_1$ through $R_5$ is independently selected from hydrogen atoms, deuterium, halogen atoms, hydroxyl groups, cyano groups, amino groups, nitro groups, carboxyl groups, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, and substituted or unsubstituted $C_2$-$C_{30}$ heterocyclic groups. Plural numbers in $R_4$ and $R_5$ are optionally the same as each other or different from each other.

Each of $Q_1$ through $Q_5$ is independently selected from hydrogen atoms, deuterium, halogen atoms, hydroxyl groups, cyano groups, amino groups, nitro groups, carboxyl groups, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, and substituted or unsubstituted $C_2$-$C_{30}$ heterocyclic groups. For example, each of $Q_1$ through $Q_5$ may be independently selected from hydrogen atoms, deuterium, halogen atoms, hydroxyl groups, cyano groups, amino groups, nitro groups, carboxyl groups, substituted or unsubstituted methyl groups, substituted or unsubstituted ethyl groups, substituted or unsubstituted propyl groups, substituted or unsubstituted butyl groups, substituted or unsubstituted pentyl groups, substituted or unsubstituted phenyl groups, substituted or unsubstituted biphenyl groups, substituted or unsubstituted pentalenyl groups, substituted or unsubstituted indenyl groups, substituted or unsubstituted naphthyl groups, substituted or unsubstituted azulenyl groups, substituted or unsubstituted heptalenyl groups, substituted or unsubstituted indacenyl groups, substituted or unsubstituted acenaphthyl groups, substituted or unsubstituted fluorenyl groups, substituted or unsubstituted spiro-fluorenyl groups, substituted or unsubstituted phenalenyl groups, substituted or unsubstituted phenanthrenyl groups, substituted or unsubstituted anthryl groups, substituted or unsubstituted fluoranthenyl groups, substituted or unsubstituted triphenylenyl groups, substituted or unsubstituted pyrenyl groups, substituted or unsubstituted chrysenyl groups, substituted or unsubstituted naphthacenyl groups, substituted or unsubstituted picenyl groups, substituted or unsubstituted perylenyl groups, substituted or unsubstituted pentaphenyl groups, substituted or unsubstituted hexacenyl groups, substituted or unsubstituted pyrrolyl groups, substituted or unsubstituted imidazolyl groups, substituted or unsubstituted pyrazolyl groups, substituted or unsubstituted pyridinyl groups, substituted or unsubstituted pyrazinyl groups, substituted or unsubstituted pyrimidinyl groups, substituted or unsubstituted pyridazinyl groups, substituted or unsubstituted isoindolyl groups, substituted or unsubstituted indolyl groups, substituted or unsubstituted indazolyl groups, substituted or unsubstituted purinyl groups, substituted or unsubstituted quinolinyl groups, substituted or unsubstituted benzoquinolinyl groups, substituted or unsubstituted phthalazinyl groups, substituted or unsubstituted naphthyridinyl groups, substituted or unsubstituted quinoxalinyl groups, substituted or unsubstituted quinazolinyl groups, substituted or unsubstituted cinnolinyl groups, substituted or unsubstituted carbazolyl groups, substituted or unsubstituted phenanthridinyl groups, substituted or unsubstituted acridinyl groups, substituted or unsubstituted phenanthrolinyl groups, substituted or unsubstituted phenazinyl groups, substituted or unsubstituted benzooxazolyl groups, substituted or unsubstituted benzoimidazolyl groups, substituted or unsubstituted furanyl groups, substituted or unsubstituted benzofuranyl groups, substituted or unsubstituted thiophenyl groups, substituted or unsubstituted benzothiophenyl groups, substituted or unsubstituted thiazolyl groups, substituted or unsubstituted isothiazolyl groups, substituted or unsubstituted benzothiazolyl groups, substituted or unsubstituted isoxazolyl groups, substituted or unsubstituted oxazolyl groups, substituted or unsubstituted triazolyl groups, substituted or unsubstituted tetrazolyl groups, substituted or unsubstituted oxadiazolyl groups, substituted or unsubstituted triazinyl groups, substituted or unsubstituted benzooxazolyl groups, substituted or unsubstituted dibenzofuranyl groups, and substituted or unsubstituted dibenzothiophenyl groups.

The condensed-cyclic compound represented by Formula 1 above includes a core, in which a fluorene moiety having good fluorescent characteristics, a carbazole moiety, a furane moiety, or a thiophene moiety is fused to an anthracene moiety having good device characteristics, and at least one triazine moiety having good electron transport capability is combined with the core.

According to an embodiment of the present invention, in the condensed-cyclic compound represented by Formula 1, a part of the core fused to an anthracene moiety may be a fluorene moiety having good fluorescent characteristics. In this case, in the condensed-cyclic compound represented by Formula 1, $X_1$ in Formula 1 may be $CR_1R_2$. For example, $X_1$ in Formula 1 may be $C(CH_3)(CH_3)$.

According to an embodiment of the present invention, $R_1$ and $R_3$ may be a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, or a substituted or unsubstituted dibenzothiophenyl group. For example, each of $R_1$ and $R_3$ may be independently selected from hydrogen atoms, deuterium, halogen atoms, hydroxyl groups, cyano groups, amino groups, nitro groups, carboxyl groups, substituted or unsubstituted methyl groups, substituted or unsubstituted ethyl groups, substituted or unsubstituted propyl groups, substituted or unsubstituted butyl groups, substituted or unsubstituted pentyl groups, substituted or unsubstituted phenyl groups, substituted or unsubstituted naphthyl groups, substituted or unsubstituted fluorenyl groups, substituted or unsubstituted spiro-fluorenyl groups, substituted or unsubstituted anthryl groups, substituted or unsubstituted pyrazolyl groups, substituted or unsubstituted pyridinyl groups, substituted or unsubstituted pyrazinyl groups, substituted or unsubstituted pyrimidinyl groups, and substituted or unsubstituted pyridazinyl groups.

According to an embodiment of the present invention, in the condensed-cyclic compound represented by Formula 1, at least one of $Ar_1$ through $Ar_{12}$ in Formula 1 may be a group represented by Formula 2 above, and more specifically, at least one selected from $Ar_1$, $Ar_3$, $Ar_4$, $Ar_6$, and $Ar_9$ may be a group represented by Formula 2 above. For example, any one or any two of $Ar_1$, $Ar_3$, $Ar_4$, $Ar_6$, and $Ar_9$ may be a group represented by Formula 2 above.

According to an embodiment of the present invention, $Ar_2$, $Ar_5$, $Ar_7$, $Ar_8$, $Ar_{10}$, $Ar_{11}$, and $Ar_{12}$ may all be hydrogen atoms, and $Ar_1$, $Ar_3$, $Ar_4$, $Ar_6$, and $Ar_9$ may each be independently selected from hydrogen atoms, deuterium, halogen atoms, hydroxyl groups, cyano groups, nitro groups, carboxyl groups, substituted or unsubstituted $C_1$-$C_{30}$ alkyl groups, substituted or unsubstituted $C_2$-$C_{30}$ alkenyl groups, substituted or unsubstituted $C_2$-$C_{30}$ alkynyl groups, substituted or unsubstituted $C_1$-$C_{30}$ alkoxy groups, substituted or unsubstituted $C_3$-$C_{30}$ cycloalkyl groups, substituted or unsubstituted $C_3$-$C_{30}$ cycloalkenyl groups, substituted or unsubstituted $C_5$-$C_{30}$ aryl groups, substituted or unsubstituted $C_5$-$C_{30}$ aryloxy groups, substituted or unsubstituted $C_5$-$C_{30}$ arylthio groups, substituted or unsubstituted $C_2$-$C_{30}$ heterocyclic groups, groups represented by Formula 2 above, groups represented by $N(Q_1)(Q_2)$, and groups represented by $Si(Q_3)(Q_4)(Q_5)$. In this case, at least one selected of $Ar_1$, $Ar_3$, $Ar_4$, $Ar_6$, and $Ar_9$ may be a group represented by Formula 2 above.

According to an embodiment of the present invention, $Ar_2$, $Ar_5$, $Ar_7$, $Ar_8$, $Ar_{10}$, $Ar_{11}$, and $Ar_{12}$ may all be hydrogen atoms, and $Ar_1$, $Ar_3$, $Ar_4$, $Ar_6$, and $Ar_9$ may each be independently selected from hydrogen atoms, deuterium, halogen atoms, hydroxyl groups, cyano groups, nitro groups, carboxyl groups, substituted or unsubstituted methyl groups, substituted or unsubstituted ethyl groups, substituted or unsubstituted propyl groups, substituted or unsubstituted butyl groups, substituted or unsubstituted pentyl groups, substituted or unsubstituted phenyl groups, substituted or unsubstituted biphenyl groups, substituted or unsubstituted pentalenyl groups, substituted or unsubstituted indenyl groups, substituted or unsubstituted naphthyl groups, substituted or unsubstituted azulenyl groups, substituted or unsubstituted heptalenyl groups, substituted or unsubstituted indacenyl groups, substituted or unsubstituted acenaphthyl groups, substituted or unsubstituted fluorenyl groups, substituted or unsubstituted spiro-fluorenyl groups, substituted or unsubstituted phenalenyl groups, substituted or unsubstituted phenanthrenyl groups, substituted or unsubstituted anthryl groups, substituted or unsubstituted fluoranthenyl groups, substituted or unsubstituted triphenylenyl groups, substituted or unsubstituted pyrenyl groups, substituted or unsubstituted chrysenyl groups, substituted or unsubstituted naphthacenyl groups, substituted or unsubstituted picenyl groups, substituted or unsubstituted perylenyl groups, substituted or unsubstituted pentaphenyl groups, substituted or unsubstituted hexacenyl groups, substituted or unsubstituted pyrrolyl groups, substituted or unsubstituted imidazolyl groups, substituted or unsubstituted pyrazolyl groups, substituted or unsubstituted pyridinyl groups, substituted or unsubstituted pyrazinyl groups, substituted or unsubstituted pyrimidinyl groups, substituted or unsubstituted pyridazinyl groups, substituted or unsubstituted isoindolyl groups, substituted or unsubstituted indolyl groups, substituted or unsubstituted indazolyl groups, substituted or unsubstituted purinyl groups, substituted or unsubstituted quinolinyl groups, substituted or unsubstituted benzoquinolinyl groups, substituted or unsubstituted phthalazinyl groups, substituted or unsubstituted naphthyridinyl groups, substituted or unsubstituted quinoxalinyl groups, substituted or unsubstituted quinazolinyl groups, substituted or unsubstituted cinnolinyl groups, substituted or unsubstituted carbazolyl groups, substituted or unsubstituted phenanthridinyl groups, substituted or unsubstituted acridinyl groups, substituted or unsubstituted phenanthrolinyl groups, substituted or unsubstituted phenazinyl groups, substituted or unsubstituted benzooxazolyl groups, substituted or unsubstituted benzimidazolyl groups, substituted or unsubstituted furanyl groups, substituted or unsubstituted benzofuranyl groups, substituted or unsubstituted thiophenyl groups, substituted or unsubstituted benzothiophenyl groups, substituted or unsubstituted thiazolyl groups, substituted or unsubstituted isothiazolyl groups, substituted or unsubstituted benzothiazolyl groups, substituted or unsubstituted isoxazolyl groups, substituted or unsubstituted oxazolyl groups, substituted or unsubstituted triazolyl groups, substituted or unsubstituted tetrazolyl groups, substituted or unsubstituted oxadiazolyl groups, substituted or unsubstituted triazinyl groups, substituted or unsubstituted benzoxazolyl groups, substituted or unsubstituted dibenzofuranyl groups, substituted or unsubstituted dibenzothiophenyl groups, and groups represented by Formula 2 above, where at least one of $Ar_1$, $Ar_3$, $Ar_4$, $Ar_6$, and $Ar_9$ may be a group represented by Formula 2 above.

The condensed-cyclic compound represented by Formula 1 above includes a core, in which a fluorene moiety, a carbazole moiety, a furane moiety, or a thiophene moiety is fused to an anthracene moiety, and a triazine moiety represented by Formula 2 is included in at least one of $Ar_1$ through $Ar_{12}$, which is a substitution product of the core. An organic light-emitting device including the condensed-cyclic compound represented by Formula 1 above has good electron transport capability due to the characteristics of the moieties.

According to an embodiment of the present invention, the condensed-cyclic compound represented by Formula 1 above includes the triazine moiety represented by Formula 2, and $L_1$ in the triazine moiety represented by Formula 2 may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenyl group, a substituted or unsubstituted naphthacenyl group, a substituted or unsubstituted picenyl group, a substituted or unsubstituted perylenylene group, a substituted or unsubstituted pentaphenylene group, and a substituted or unsubstituted hexylenylene group.

According to an embodiment of the present invention, a in Formula 2 above may be 0 or 1. When a is 0, it indicates a simple single combination. When a is 0 or 1, the condensed-cyclic compound represented by Formula 1 above may have good electron transport capability.

According to an embodiment of the present invention, each of $R_4$ through $R_8$ in Formula 2 may independently be a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted indenoanthracenyl group, a substituted or unsubstituted pyrazolyl group, a substituted or unsubstituted pyridinyl group, a substituted or unsubstituted bipyridinyl group, a substituted or unsubstituted pyridazinyl group, a substituted or unsubstituted pyrimidinyl group, a substituted or unsubstituted pyrazinyl group, a substituted or unsubstituted quinolinyl group, or a substituted or unsubstituted phenanthrolinyl group. For example, $R_4$ and $R_5$ may be the same as each other and each may be a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted indenoanthracenyl group, a substituted or unsubstituted pyrazolyl group, a substituted or unsubstituted pyridinyl group, a substituted or unsubstituted bipyridinyl group, a substituted or unsubstituted pyridazinyl group, a substituted or unsubstituted pyrimidinyl group, a substituted or unsubstituted pyrazinyl group, a substituted or unsubstituted quinolinyl group, or a substituted or unsubstituted phenanthrolinyl group.

In the condensed-cyclic compound represented by Formula 1, the group represented by Formula 2 above may be a condensed-cyclic compound represented by one of Formulas 2A through 2U below:
Formula 2A
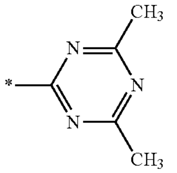
Formula 2B
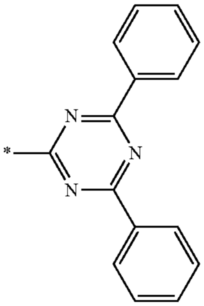
Formula 2C
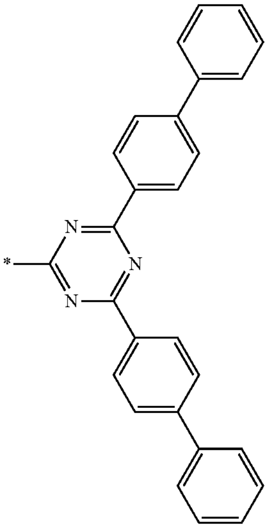
Formula 2D
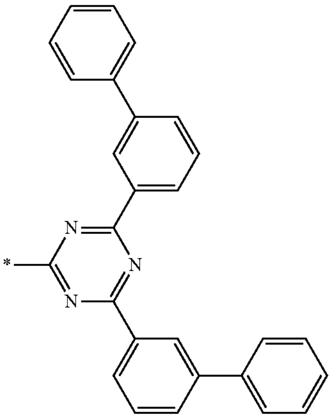
-continued
Formula 2E
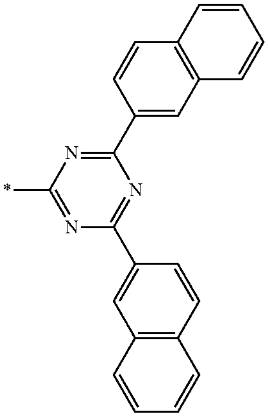
Formula 2F
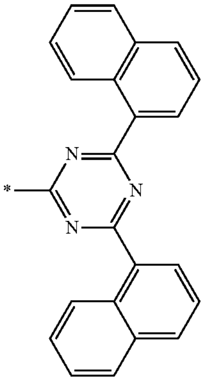
Formula 2G
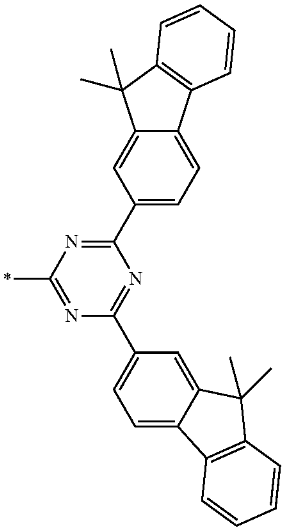

-continued
Formula 2H
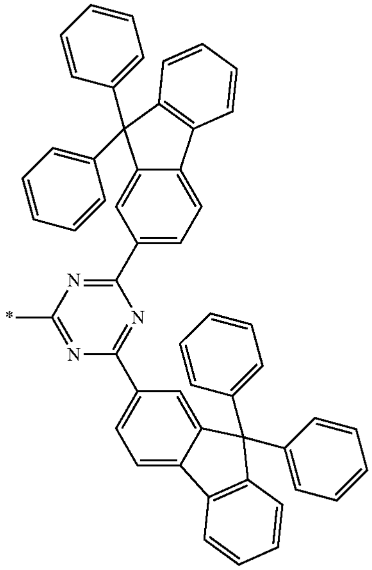
Formula 2I
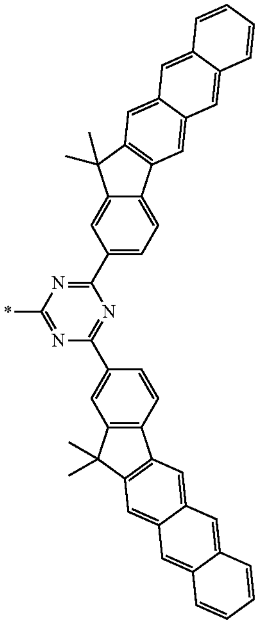
-continued
Formula 2J
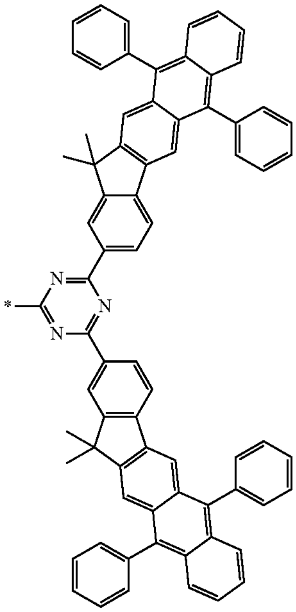
Formula 2K
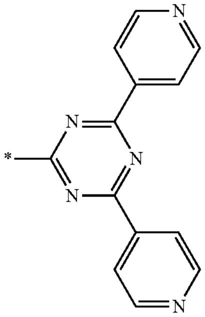
Formula 2L
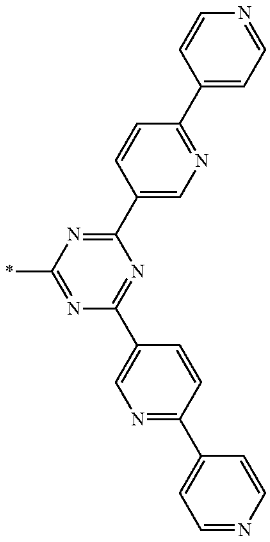

-continued
Formula 2M
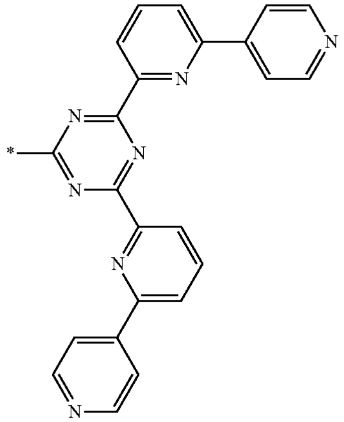
Formula 2N
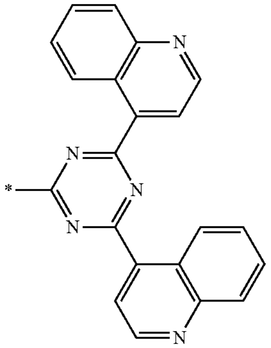
Formula 2O
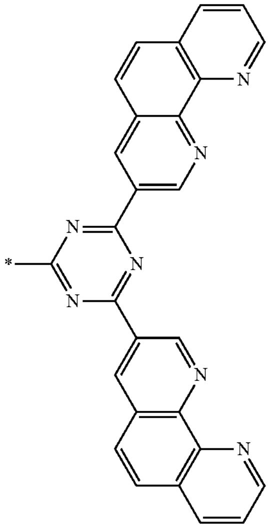
Formula 2P
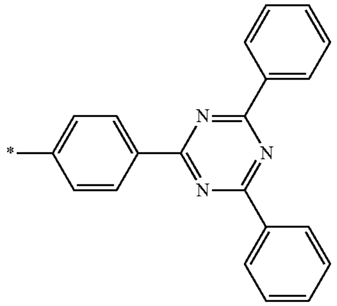
-continued
Formula 2Q
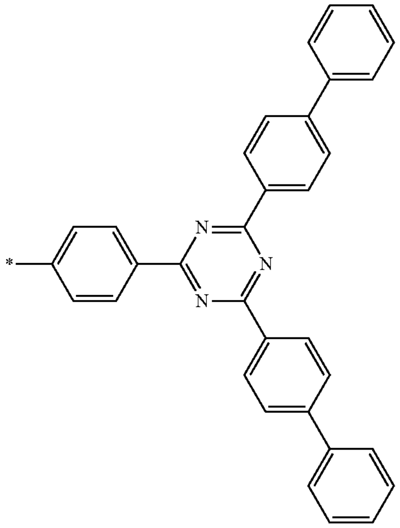
Formula 2R
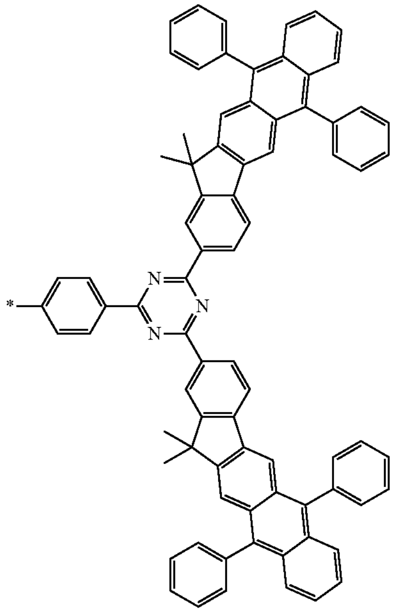
Formula 2S
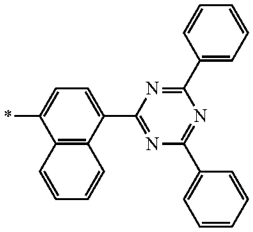

-continued
Formula 2T
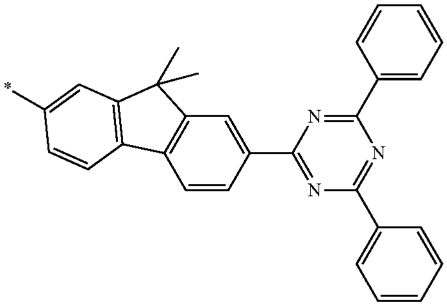
-continued
Formula 2U
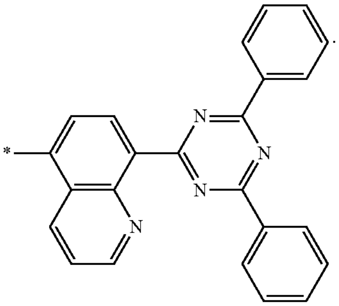
Nonlimiting examples of the condensed-cyclic compound represented by Formula 1 include the compounds represented by Compounds 1 through 40 below:
Compound 1
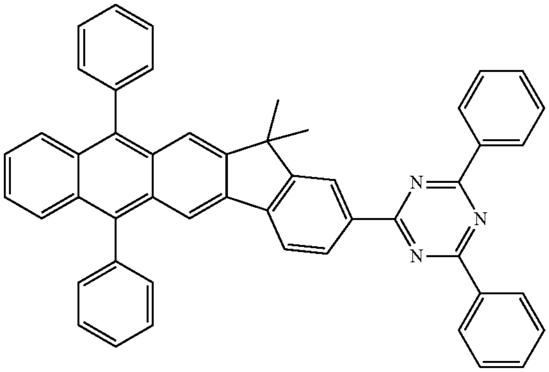
Compound 2
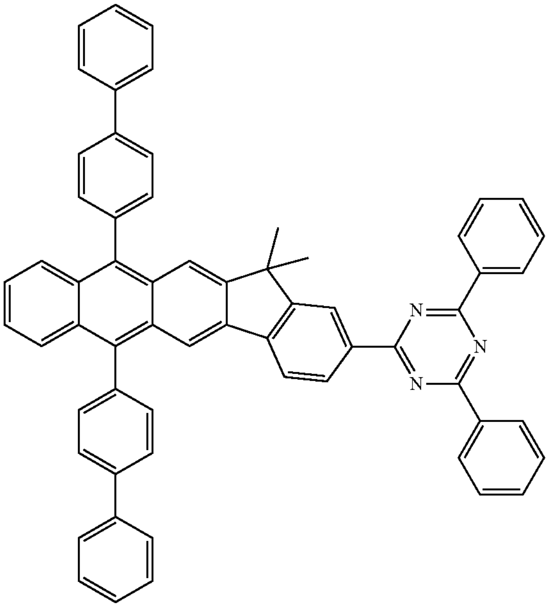
Compound 3
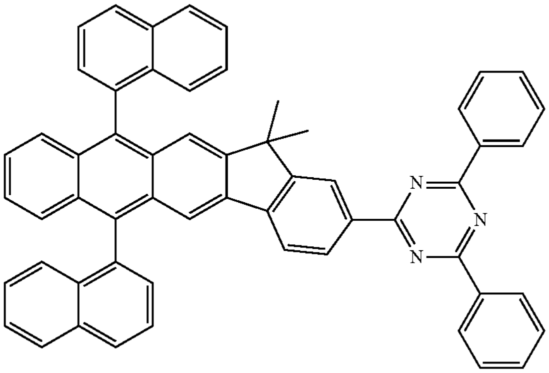
Compound 4
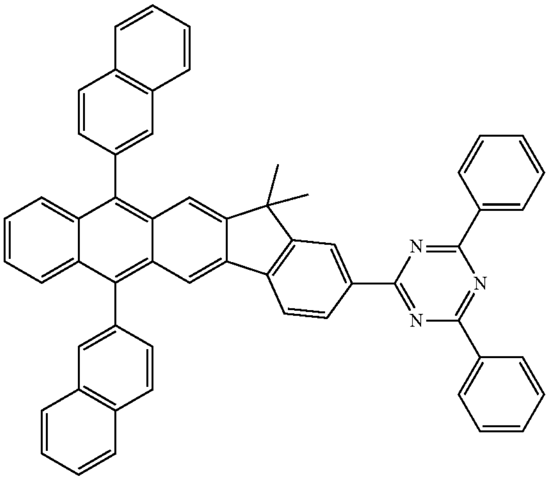

-continued
Compound 5
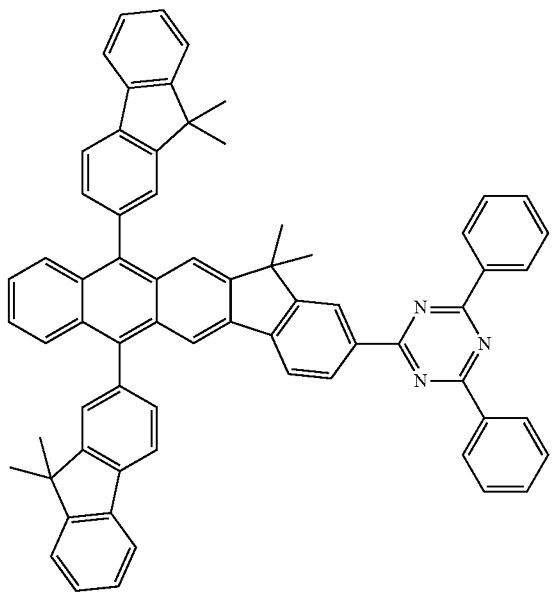
Compound 6
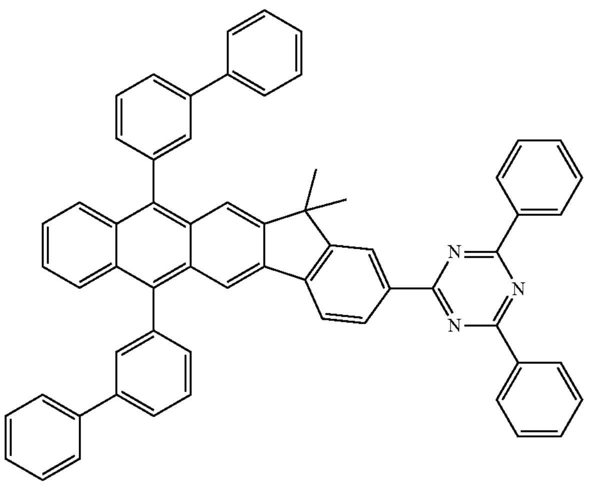
Compound 7
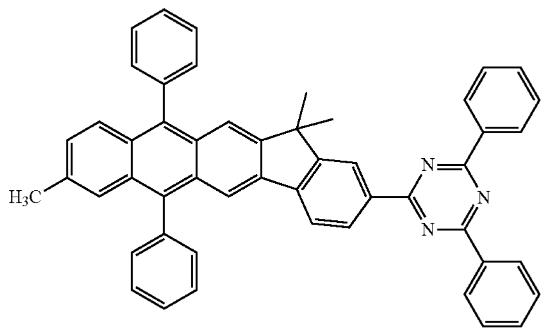
Compound 8
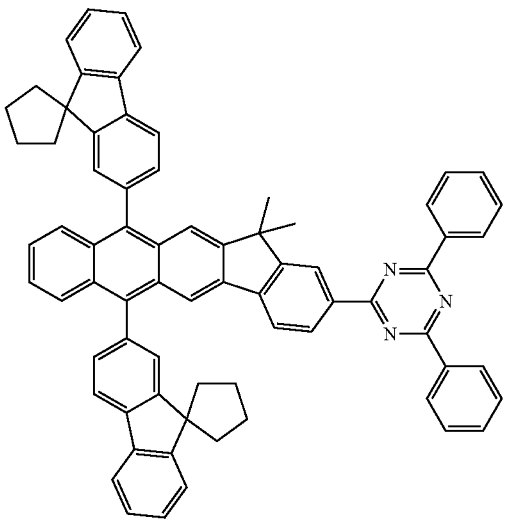
Compound 9
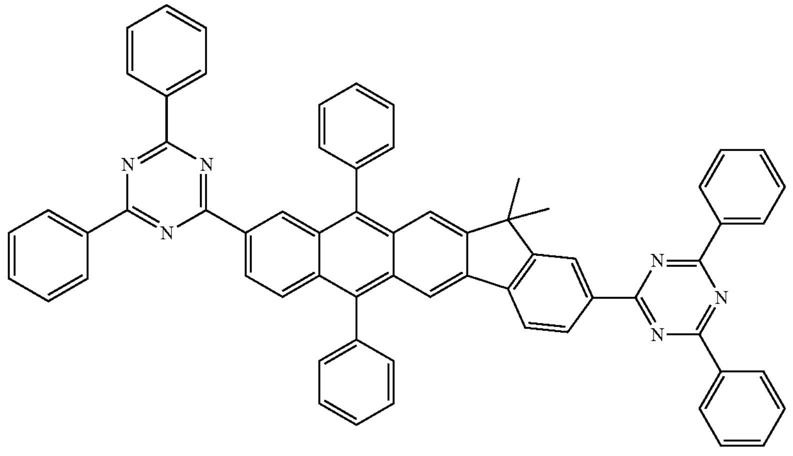

-continued
Compound 10
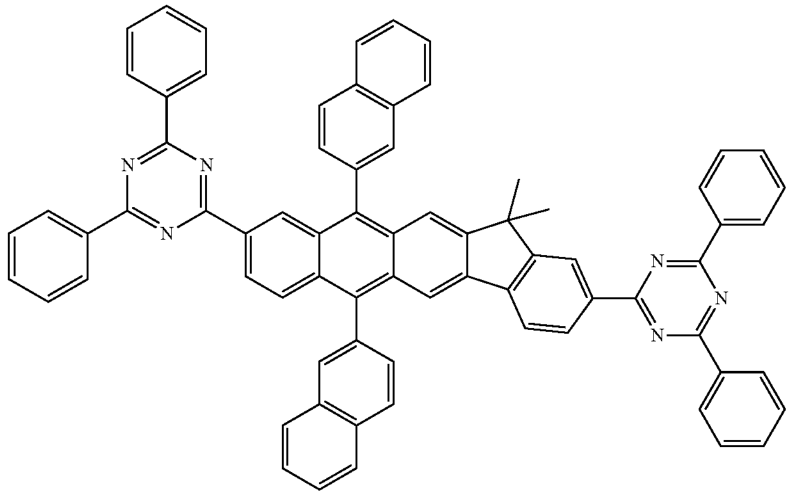
Compound 11
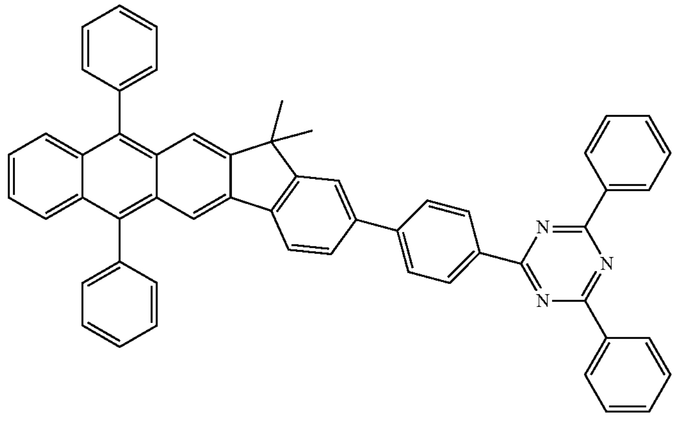
Compound 12
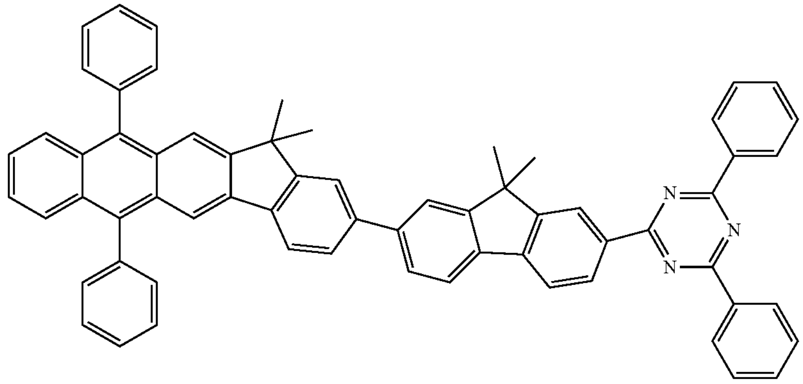

-continued
Compound 13
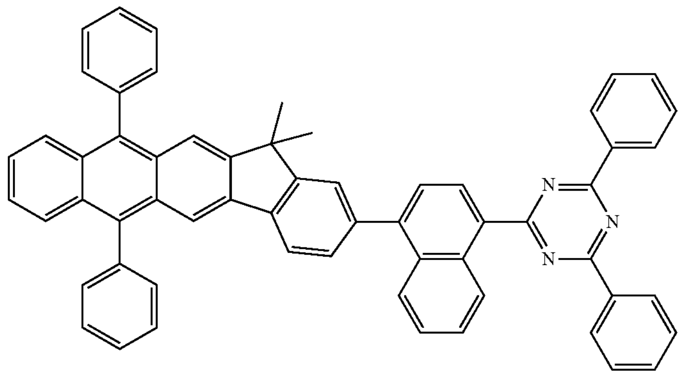
Compound 14
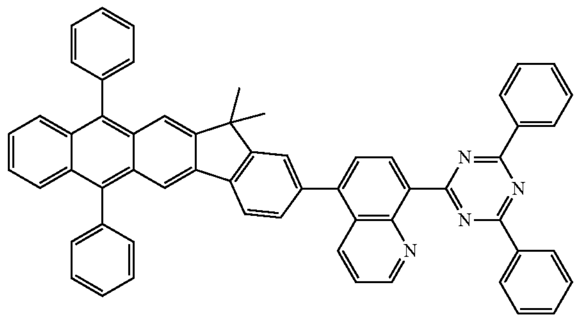
Compound 15
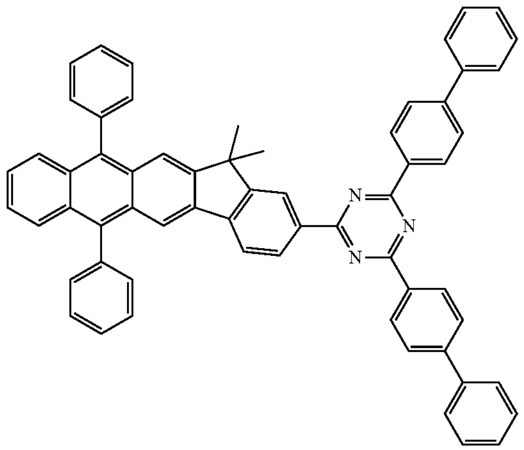
Compound 16
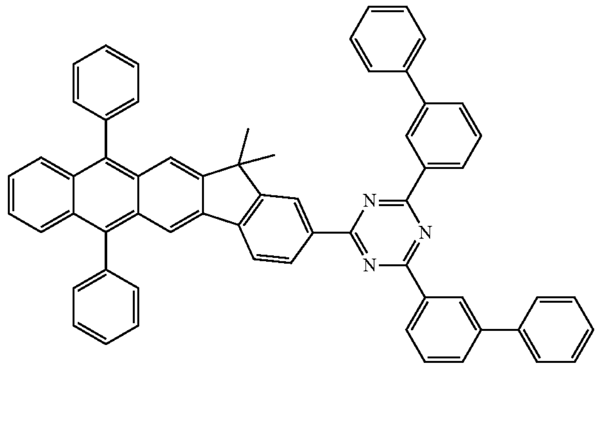
Compound 17
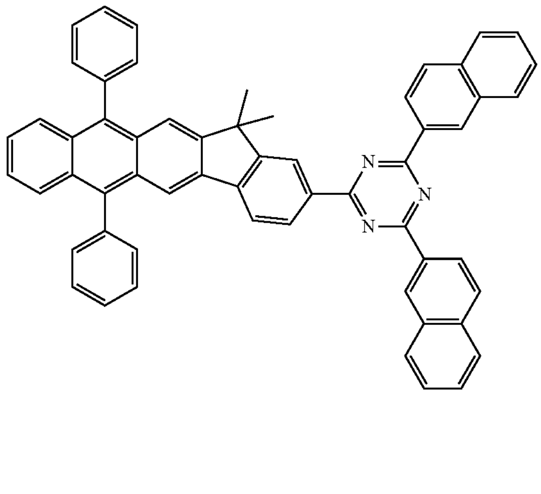

-continued
Compound 18
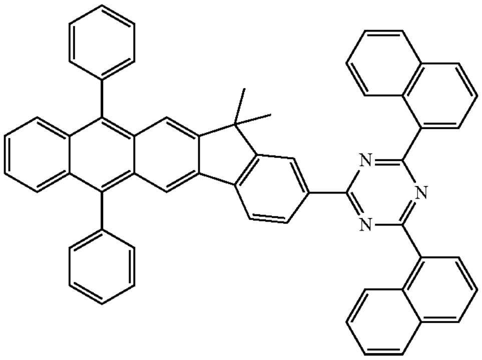
Compound 19
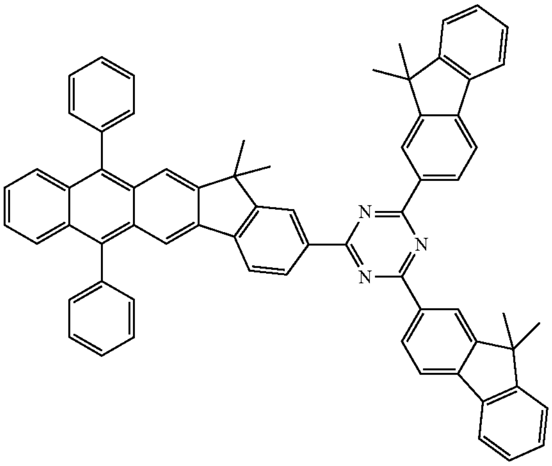
Compound 20
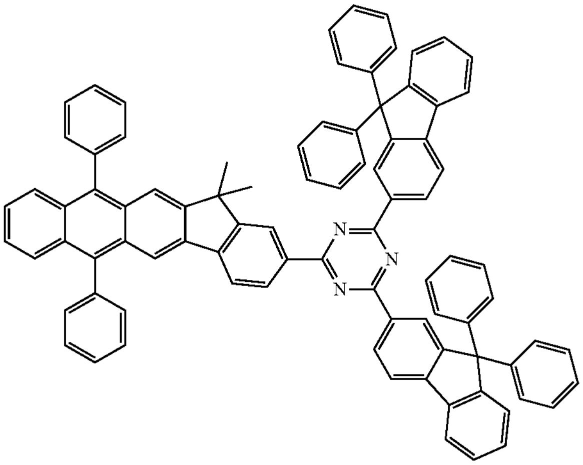
Compound 21
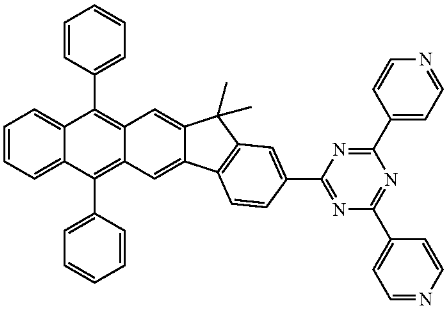
Compound 22
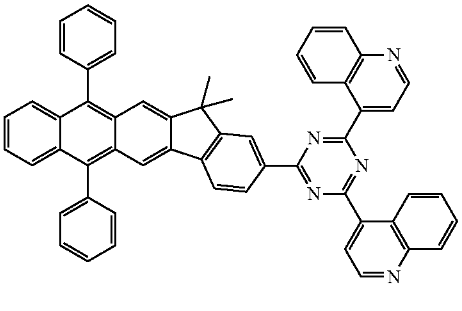
Compound 23
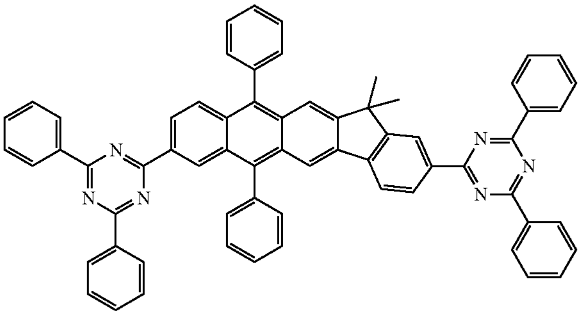

-continued
Compound 24
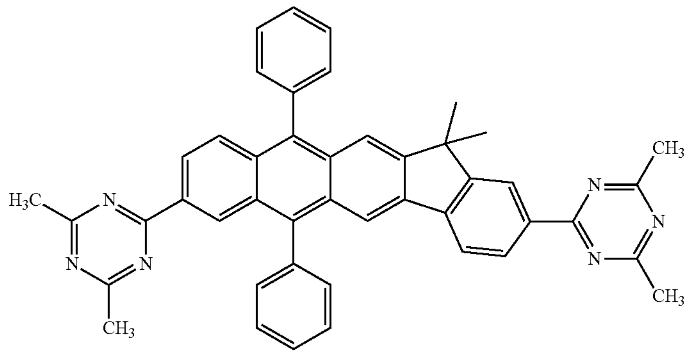
Compound 25
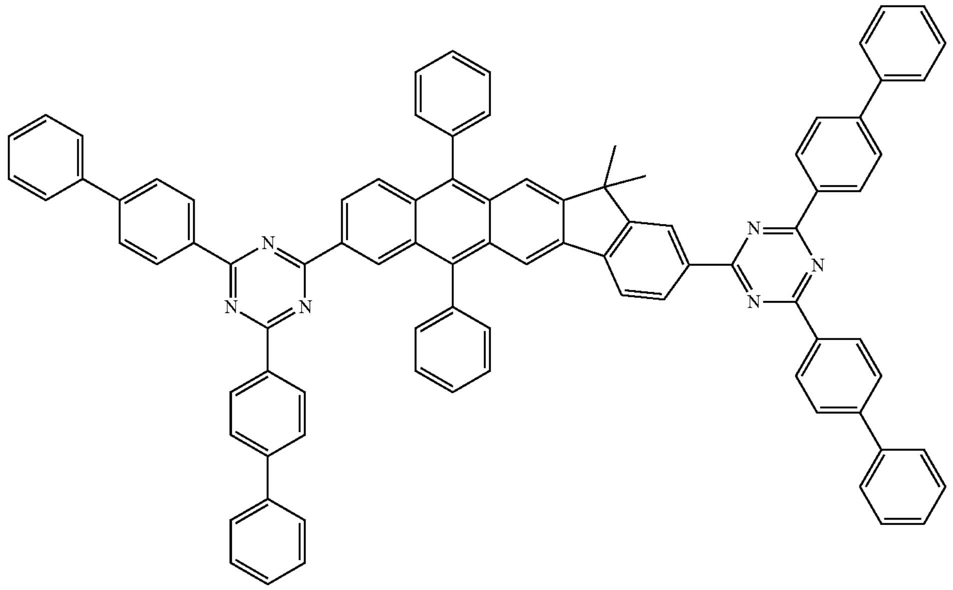
Compound 26
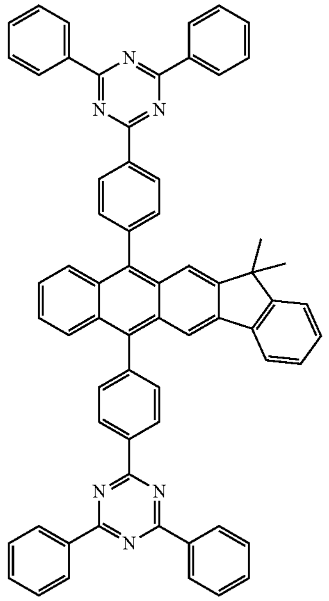
Compound 27
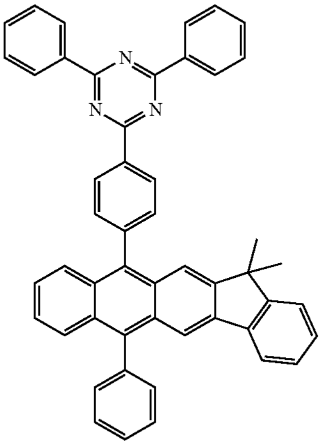

-continued
Compound 28
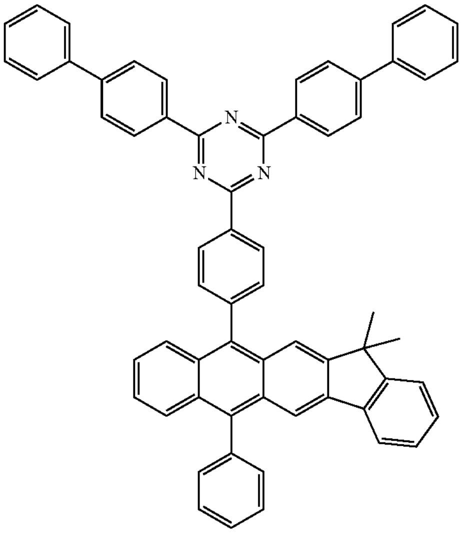
Compound 29
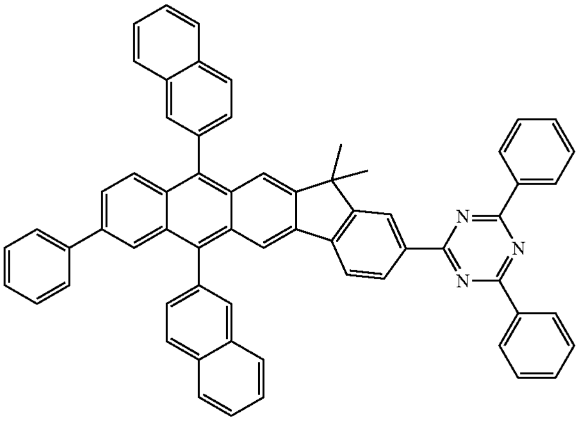
Compound 30
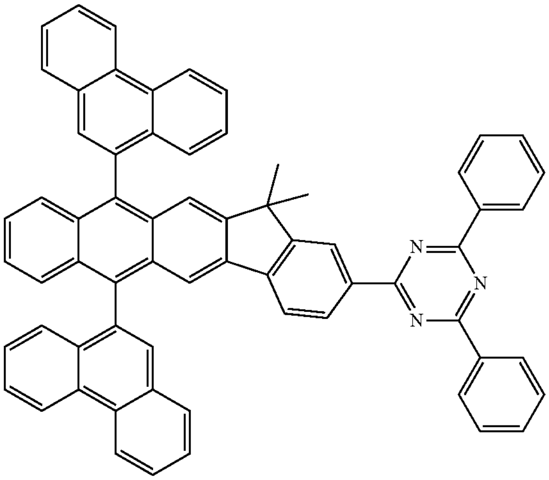
Compound 31
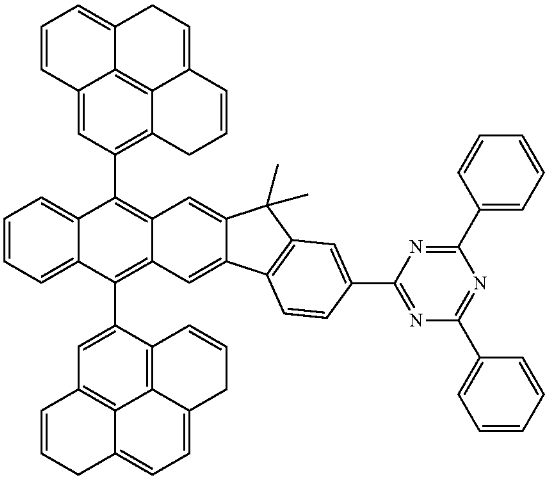
Compound 32
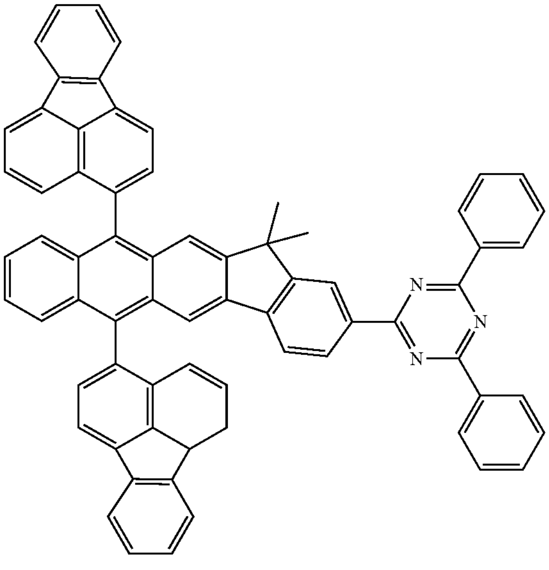

-continued
Compound 33
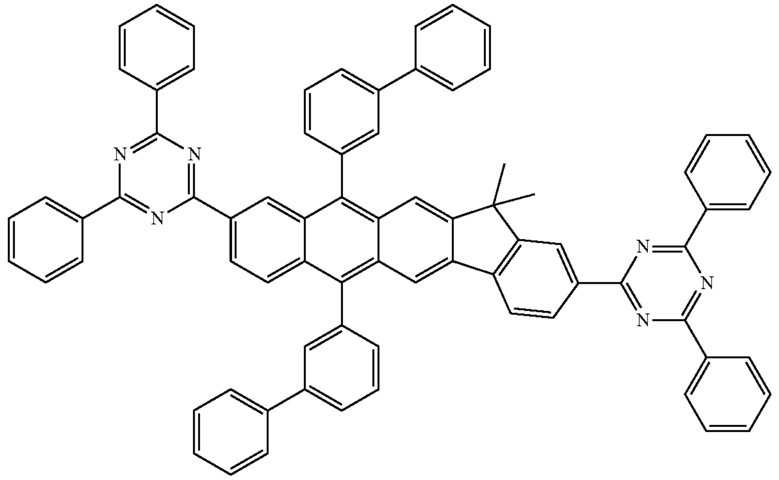
Compound 34
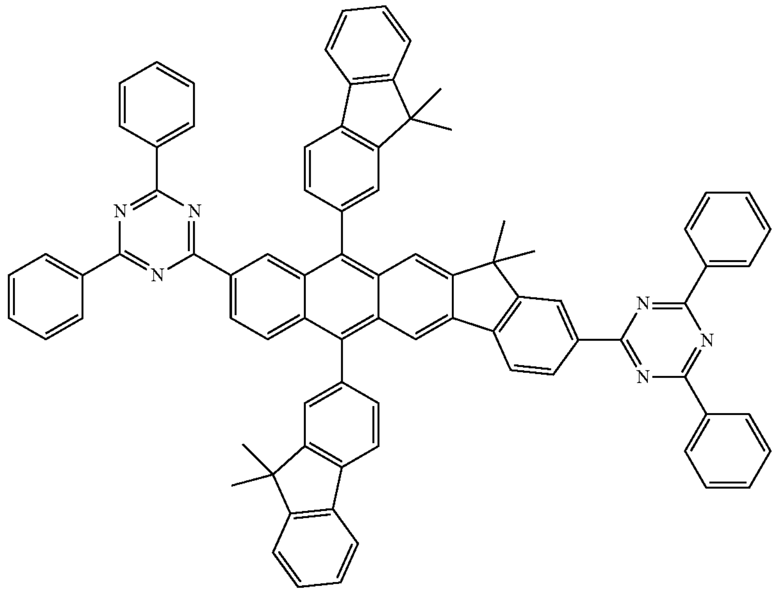
Compound 35
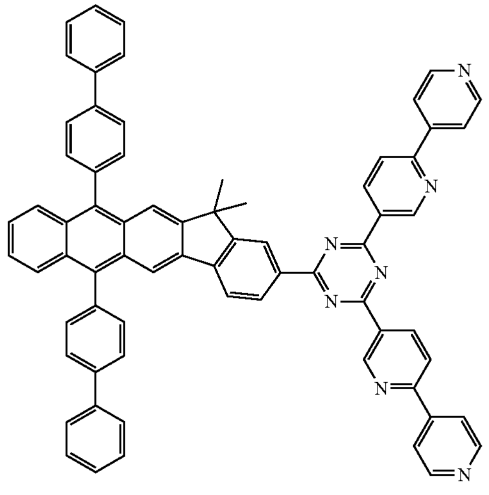
Compound 36
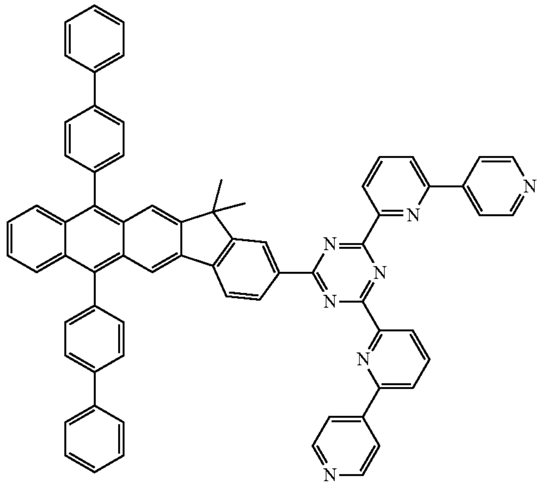

-continued
Compound 37
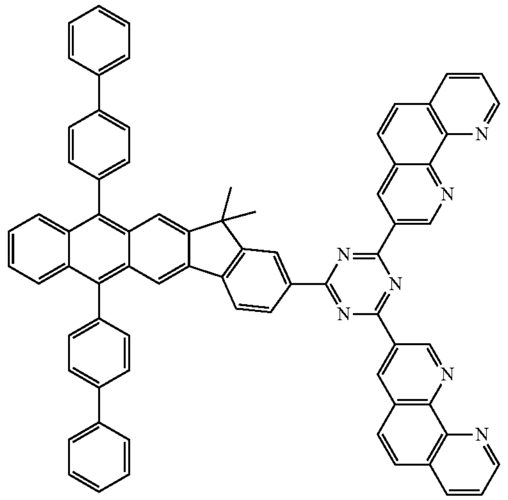
Compound 38
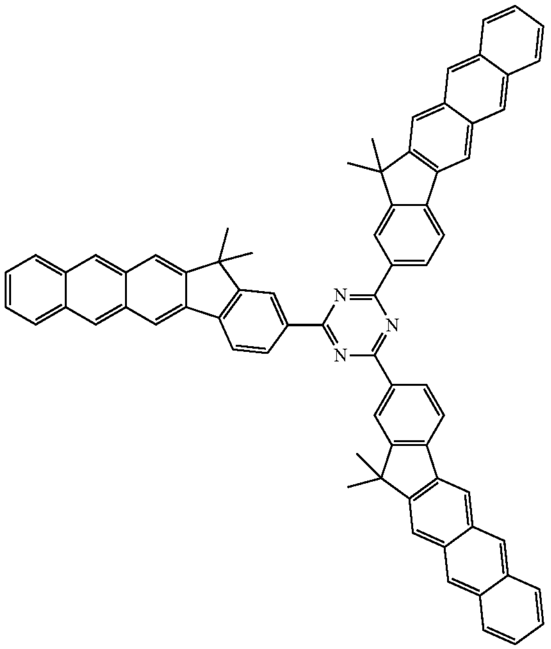
Compound 39
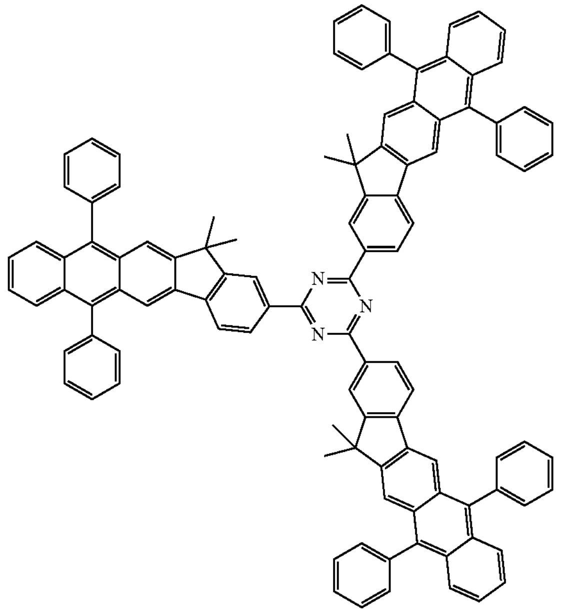

-continued

Compound 40

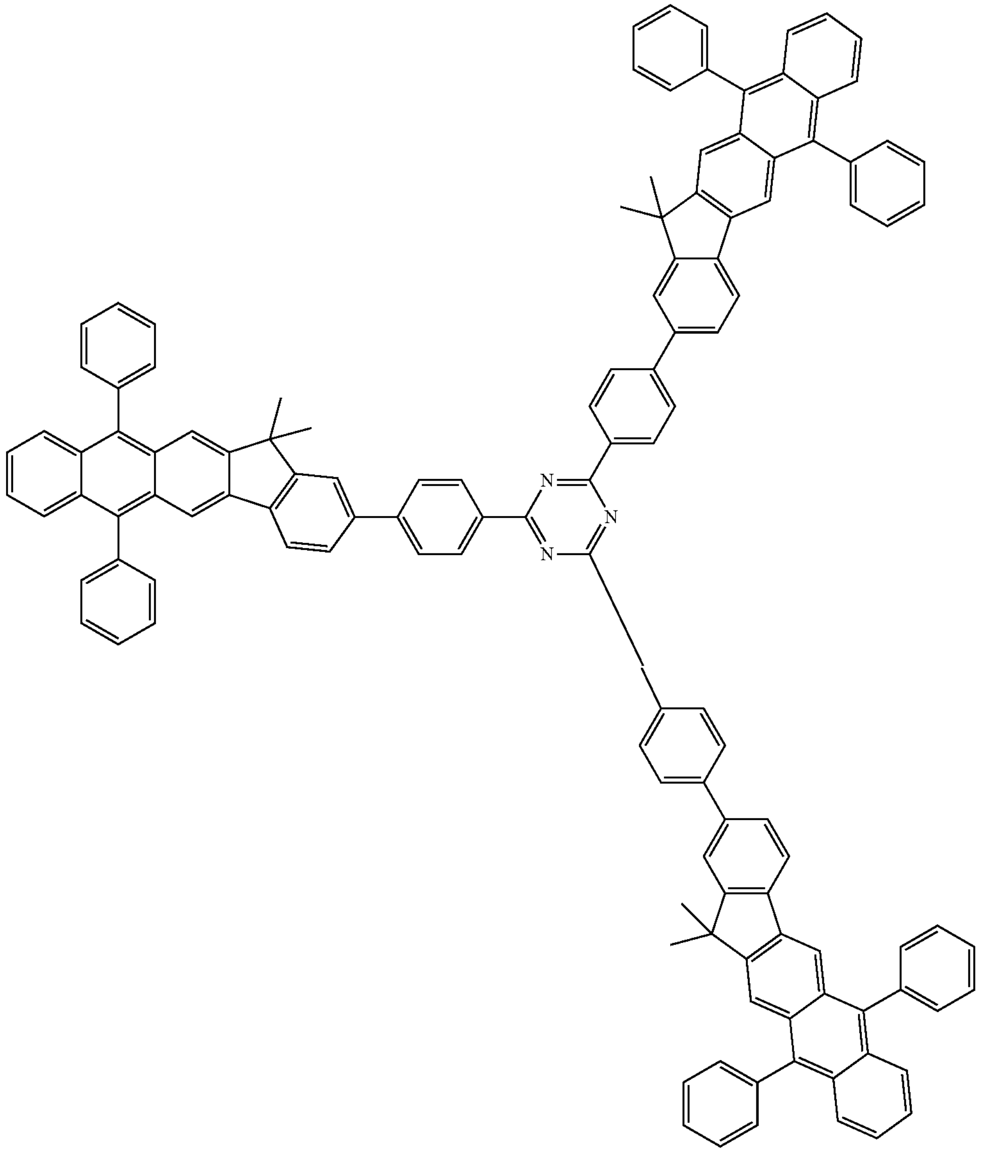

In the expression "substituted or unsubstituted A (in which A is an arbitrary substituent)," the term "substituted A" denotes "A, in which at least one hydrogen atom of A is substituted with a substituent selected from deuterium, halogen atoms, hydroxyl groups, cyano groups, nitro groups, carboxyl groups or salt derivatives thereof, sulfonic acid groups or salt derivatives thereof, phosphate groups or salt derivatives thereof, $C_1$-$C_{30}$ alkyl groups, $C_2$-$C_{30}$ alkenyl groups, $C_2$-$C_{30}$ alkynyl groups, $C_1$-$C_{30}$ alkoxy groups, $C_3$-$C_{30}$ cycloalkyl groups, $C_3$-$C_{30}$ cycloalkenyl groups, $C_5$-$C_{30}$ aryl groups, $C_5$-$C_{30}$ aryloxy groups, $C_5$-$C_{30}$ arylthio groups, $C_2$-$C_{30}$ heterocyclic groups, groups represented by $N(Q_{101})(Q_{102})$, and groups represented by $Si(Q_{103})(Q_{104})(Q_{105})$." Here, each of $Q_{101}$ through $Q_{105}$ may independently be a hydrogen atom, deuterium, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, or a $C_2$-$C_{30}$ heterocyclic group.

For example, "the substituted A" may denote "A, in which at least one hydrogen atom is substituted with deuterium, a halogen atom, a hydroxyl group, a cyano group, an amino group, a nitro group, a carboxyl group, a substituted or unsubstituted a methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group a substituted or unsubstituted benzoxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzoxazolyl group, a substituted or unsubstituted dibenzofuranyl group, or a substituted or unsubstituted dibenzothiophenyl group."

The unsubstituted $C_1$-$C_{30}$ alkyl group denotes a saturated hydrocarbon group having a linear or branched structure in which one hydrogen atom is missing from the corresponding alkane. Nonlimiting examples of the unsubstituted $C_1$-$C_{30}$ alkyl group may include methyl, ethyl, propyl, isobutyl, sec-butyl, pentyl, iso-amyl, hexyl, and the like. The substituents of the substituted $C_1$-$C_{30}$ alkyl group are described in the description for the "substituted A."

The unsubstituted $C_2$-$C_{30}$ alkenyl group denotes a $C_2$-$C_{30}$ alkyl group having at least one carbon-carbon double bond at the middle or end. Nonlimiting examples of the unsubstituted $C_2$-$C_{30}$ alkenyl group may include ethenyl, prophenyl, butenyl, pentanyl, hexenyl, heptenyl, octenyl, propadienyl, isoprenyl, allyl, and the like. The substituents of the substituted $C_2$-$C_{30}$ alkenyl group are described in the description for the "substituted A."

The unsubstituted $C_2$-$C_{30}$ alkynyl group denotes a $C_2$-$C_{60}$ alkyl group having at least one carbon-carbon triple bond at the middle or end. Nonlimiting examples of the unsubstituted $C_2$-$C_{30}$ alkynyl group may include acetylenyl groups. The substituents of the substituted $C_2$-$C_{30}$ alkynyl group are described in the description for the "substituted A."

The unsubstituted $C_1$-$C_{30}$ alkoxy group has the Formula —OY (in which Y is the unsubstituted $C_1$-$C_{30}$ alkyl group) and may be, for example, methoxy, ethoxy, isopropyloxy, butoxy, pentoxy, and the like. The substituents of the substituted $C_1$-$C_{30}$ alkoxy group are described in the description for the "substituted A."

The unsubstituted $C_3$-$C_{30}$ cycloalkyl group denotes a ring-type saturated hydrocarbon group and may be, for example, cyclopropyl, cyclobutyl, cyclopentyl, cyclohexyl, cyclooctyl, and the like. The substituents of the substituted $C_3$-$C_{30}$ cycloalkyl group are described in the description for the "substituted A."

The unsubstituted $C_3$-$C_{30}$ cycloalkenyl group denotes a ring-type unsaturated hydrocarbon group which has at least one carbon-carbon double bond but is not an aromatic ring. Nonlimiting examples of the unsubstituted $C_3$-$C_{30}$ cycloalkenyl group include cyclopropenyl groups, cyclobutenyl groups, cyclopentenyl groups, cyclohexenyl groups, cycloheptenyl groups, 1,3-cyclohexadienyl groups, 1,4-cyclohexadienyl groups, 2,4-cycloheptadienyl groups, 1,5-cyclooctadienyl groups, and the like. The substituents of the substituted $C_3$-$C_{60}$ cycloalkenyl group are described in the description for the "substituted A."

The unsubstituted $C_5$-$C_{30}$ aryl group denotes a monovalent group having a $C_5$-$C_{30}$ carbocyclic aromatic system, wherein the monovalent group may be a monocyclic or polycyclic group. In the polycyclic group, at least two rings included therein may be fused to each other. Nonlimiting examples of the unsubstituted $C_5$-$C_{30}$ aryl group may include phenyl, pentalenyl, indenyl, naphthyl, azulenyl, heptalenyl, indacenyl, acenaphthyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, hexacenyl, and the like. The substituents of the substituted $C_5$-$C_{30}$ aryl group are described in the description for the "substituted A."

The unsubstituted $C_5$-$C_{30}$ aryloxy group denotes a monovalent group to which carbon atoms of a $C_5$-$C_{30}$ aryl group are attached through an oxygen linking group (—O—). The substituents of the substituted $C_5$-$C_{30}$ aryloxy group are described in the description for the "substituted A."

The unsubstituted $C_5$-$C_{30}$ arylthio group denotes a monovalent group to which carbon atoms of a $C_5$-$C_{30}$ aryl group are attached through a sulfur linking group (—S—). Nonlimiting examples of the unsubstituted $C_5$-$C_{30}$ arylthio group include phenylthio, naphthylthio, indanylthio, and indenylthio. The substituents of the substituted $C_5$-$C_{30}$ arylthio group are described in the description for the "substituted A."

The unsubstituted $C_2$-$C_{30}$ heterocyclic group denotes a monocyclic or polycyclic group including at least one ring containing at least one heteroatom selected from N, O, P, and S. In the polycyclic group, at least two rings included therein may be fused to each other. Nonlimiting examples of the unsubstituted $C_2$-$C_{30}$ heterocyclic group include pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazole, oxadiazolyl, triazinyl, benzooxazolyl, and the like. The substituents of the substituted $C_2$-$C_{30}$ heterocyclic group are described in the description for the "substituted A."

The unsubstituted $C_1$-$C_{30}$ alkylene group denotes a divalent group having a linear or chain structure, in which two hydrogen atoms are missing from the corresponding alkane.

Nonlimiting examples of the unsubstituted $C_1$-$C_{30}$ alkylene group would be understood to those of ordinary skill in the art by reference to the examples for the unsubstituted $C_1$-$C_{30}$ alkyl group. The substituents of the substituted $C_1$-$C_{30}$ alkylene group are described in the description for the "substituted A."

The unsubstituted $C_5$-$C_{30}$ arylene group denotes a divalent group having a $C_5$-$C_{30}$ carbocyclic aromatic system, where the divalent group may be a monocyclic or polycyclic group. Nonlimiting examples of the unsubstituted $C_5$-$C_{30}$ arylene group may be understood to those of ordinary skill in the art by reference to the examples for the unsubstituted $C_5$-$C_{30}$ aryl group. The substituents of the substituted $C_5$-$C_{30}$ arylene group are described in the description for the "substituted A."

The unsubstituted divalent $C_2$-$C_{30}$ heterocyclic group denotes a monocyclic or polycyclic divalent group including at least one ring containing at least one heteroatom selected from N, O, P, and S, and may be a monocyclic or a polycyclic group. Nonlimiting examples of the unsubstituted divalent $C_2$-$C_{30}$ heterocyclic group may be understood to those of ordinary skill in the art by reference to the examples for the unsubstituted $C_2$-$C_{30}$ heterocyclic group. The substituents of the substituted divalent $C_2$-$C_{30}$ heterocyclic group are described in the description for the "substituted A."

The condensed-cyclic compound represented by Formula 1 may be synthesized using known organic synthesis methods. The synthesis method of the condensed-cyclic compound would be readily recognized by one of ordinary skill in the art with reference to the Examples which are described below.

The condensed-cyclic compound represented by Formula 1 may be used in an organic light-emitting device. That is, according to embodiments of the present invention, an organic light-emitting device includes a first electrode, a second electrode facing the first electrode, and at least one organic layer between the first electrode and the second electrode, where the at least one organic layer includes the condensed-cyclic compound represented by Formula 1.

The organic layer may be an electron injection layer, an electron transport layer, or a functional layer having both electron injection and electron transport functions. For example, in the organic light-emitting device, the organic layer including the condensed-cyclic compound represented by Formula 1 may be an electron transport layer.

The organic layer may be a hole injection layer, a hole transport layer or a single layer simultaneously having hole injection and hole transport functions.

Also, the organic layer may be an emission layer in an organic light-emitting device and may include the condensed-cyclic compound represented by Formula 1. More specifically, the emission layer may include only the condensed-cyclic compound represented by Formula 1, or may further include another compound in addition to the condensed-cyclic compound represented by Formula 1.

For example, the condensed-cyclic compound represented by Formula 1 may be used as a fluorescent host or a phosphorescent host in the emission layer. In this case, the emission layer may further include a fluorescent dopant or a phosphorescent dopant. That is, the emission layer may include the condensed-cyclic compound represented by Formula 1 functioning as a fluorescent host and further include a compound functioning as a fluorescent dopant. Alternatively the emission layer may include the condensed-cyclic compound represented by Formula 1 functioning as a phosphorescent host and further include a compound functioning as a phosphorescent dopant.

Also, the condensed-cyclic compound represented by Formula 1 may be used as a fluorescent dopant of the emission layer. In this case, the emission layer may further include a fluorescent host or a phosphorescent host, in addition to the condensed-cyclic compound represented by Formula 1. That is, the emission layer may include the condensed-cyclic compound represented by Formula 1 functioning as a fluorescent dopant and further include a compound functioning as a phosphorescent host or a fluorescent host.

The organic light-emitting device may further include at least one of a hole injection layer, a hole transport layer, an electron blocking layer, a hole blocking layer, an electron transport layer, and an electron injection layer between the first electrode and the second electrode, in addition to the emission layer.

For example, the organic light-emitting device may have a first electrode/hole injection layer/emission layer/electron transport layer/electron injection layer/second electrode structure, a first electrode/hole injection layer/hole transport layer/emission layer/electron transport layer/electron injection layer/second electrode structure, or a first electrode/hole injection layer/hole transport layer/emission layer/hole blocking layer/electron transport layer/electron injection layer/second electrode structure. However, the present invention is not limited thereto.

The at least one layer between the first electrode and the second electrode may be formed by deposition or a wet process. For example, at least one of a hole injection layer, a hole transport layer, an emission layer, a hole blocking layer, an electron transport layer, and an electron injection layer between the first electrode and the second electrode may be formed by deposition or a wet process.

As used herein, "wet process" is a process for obtaining a mixture by mixing a predetermined material with a predetermined solvent, applying the mixture to a predetermined substrate, and drying and/or thermally treating the predetermined substrate to remove at least part of the predetermined solvent, thereby forming a film including the predetermined material on the substrate.

In the wet process, the organic layer including the condensed-cyclic compound represented by Formula 1 may be applied to the substrate by general vacuum deposition. For example, a mixture of the condensed-cyclic compound represented by Formula 1 and the solvent are applied to an electron transport layer region by spin coating, spraying, inkjet printing, dipping, casting, gravure coating, bar coating, roll coating, wirebar coating, screen coating, flexo coating, offset coating, or laser transferring, and then the mixture applied to the electron transport layer region is dried and/or heat treated to remove at least part of the solvent. Thus, the electron transport layer including the condensed-cyclic compound represented by Formula 1 may be formed.

Also, a layer including the condensed-cyclic compound represented by Formula 1 may be formed on the base film by using a wet process, and the layer may be transferred on the electron transport layer region by laser transferring using laser.

FIG. 1 is a schematic cross-sectional view of an organic light-emitting device 10 according to an embodiment of the present invention. Hereinafter, a structure and a manufacturing method of the organic light-emitting device 10 will be described with reference to FIG. 1.

The organic light-emitting device 10 includes a first electrode 12, a hole injection layer 13, a hole transport layer 14, an emission layer 15, an electron transport layer 16, an electron injection layer 17, and a second electrode 18 sequentially on a substrate 11 in this order.

The substrate 11 may be any substrate generally used in organic light-emitting devices, and may be, for example, a glass substrate or a transparent plastic substrate having good mechanical strength, thermal stability, transparency, surface smoothness, ease of handling, and waterproofness.

The first electrode 12 may be formed by providing a first electrode material on the substrate 11 using deposition or sputtering. When the first electrode 12 is an anode, the first electrode material may be selected from materials having a high work function so as to facilitate hole injection. The first electrode 12 may be a reflective electrode or a transparent electrode. Nonlimiting examples of the first electrode material include indium-tin oxide (ITO), Indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used, the first electrode 12 may be formed as a reflective electrode. The first electrode 12 may include two different materials. The structure of the first electrode 12 may vary and, for example, the first electrode 12 may be formed to have a two-layered structure including two different materials.

The hole injection layer 13 is formed on the first electrode 12.

The hole injection layer 13 may be formed on the first electrode 12 by any of various methods such as vacuum deposition, a wet process, or laser transferring.

When the hole injection layer 13 is formed by using vacuum deposition, the deposition conditions may vary according to the compound used as the material for the hole injection layer, the structure of the desired hole injection layer, and the thermal characteristics. For example, the deposition conditions may be, but are not limited to, a deposition temperature of about 100 to about 500° C., a degree of vacuum of about $10^{-8}$ to about $10^{-3}$ torr, and a deposition speed of about 0.01 to about 100 Å/sec.

When the hole injection layer 13 is formed by spin coating and a wet process, the coating conditions may vary according to the compound used as the material for the hole injection layer, the structure of the desired hole injection layer, and the thermal characteristics. For example, the coating conditions may be, but are not limited to, a coating speed of about 2000 rpm to about 5000 rpm and a heat treatment temperature for removing the solvent after coating of about 80 to about 200° C.

The condensed-cyclic compound may be used as the material for a hole injection layer. Also, the material for the hole injection layer may include at least one of the condensed-cyclic compound and a known material for the hole injection layer and may include, for example, a phthalocyanine compound such as copper phthalocyanine, m-MTDATA (refer to Formula below), TDATA (refer to Formula below), 2-TNATA (refer to Formula below), Polyaniline/Dodecylbenzenesulfonic acid (Pani/DBSA), Poly(3,4-ethylenedioxythiophene)/Poly(4-styrenesulfonate) (PEDOT/PSS), Polyaniline/Camphor sulfonicacid (Pani/CSA), or Polyaniline/Poly(4-styrenesulfonate) (PANI/PSS). However, the present invention is not limited thereto.

m-MTDATA

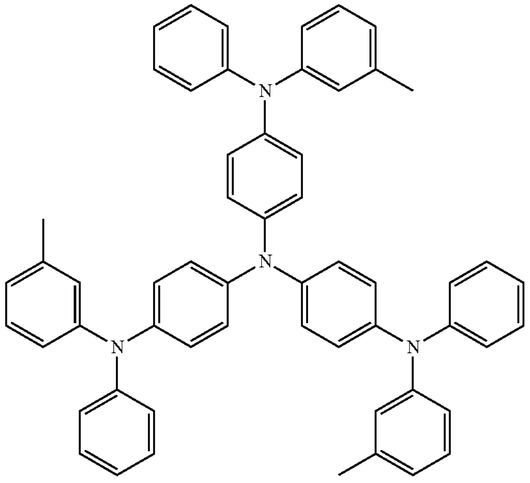

TDATA

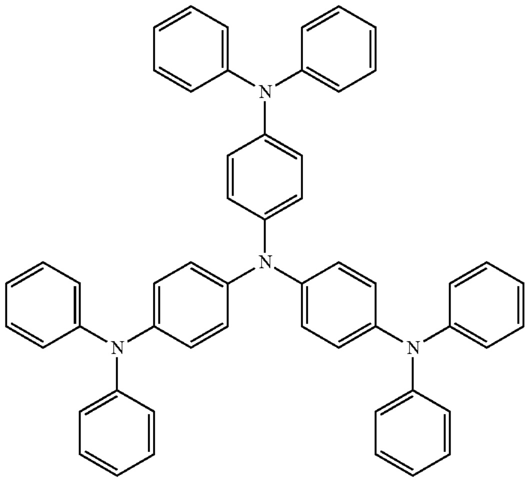

2-TNATA

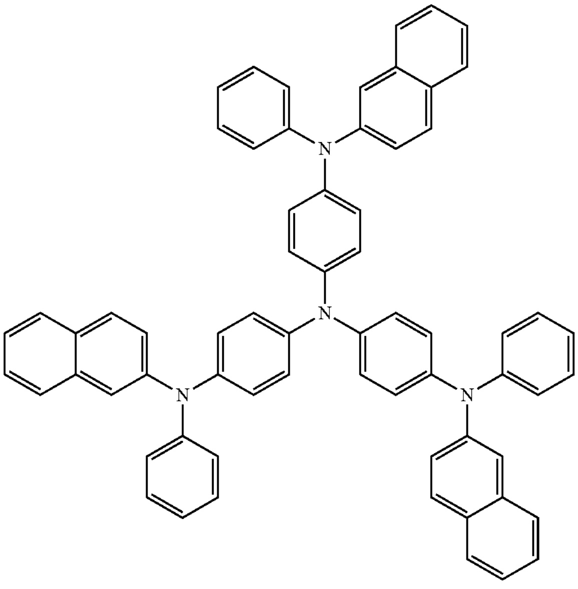

A thickness of the hole injection layer 13 may be about 100 Å to about 10000 Å, for example, about 100 Å to about 1000

Å. When the thickness of the hole injection layer 13 is within these ranges, satisfactory hole injection characteristics may be obtained without a substantial increase in the driving voltage.

The hole transport layer 14 is formed on the hole injection layer 13 by vacuum deposition, a wet process, or laser transferring. When the hole transport layer 14 is formed by vacuum deposition or spin coating, the deposition conditions and coating conditions may vary according to the compound used. However, in general, the conditions may be similar to the conditions described above for forming the hole injection layer 13.

The hole transport layer 14 may include any known material for the hole transport layer, for example, TPD (refer to Formula below) or NPB (refer to Formula below).

TPD

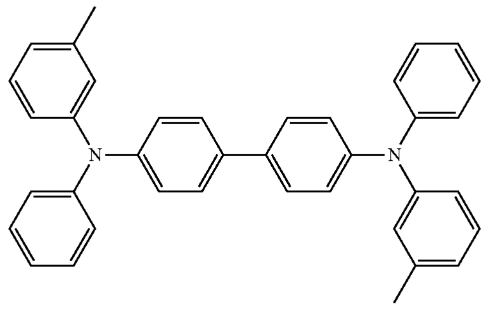

NPB

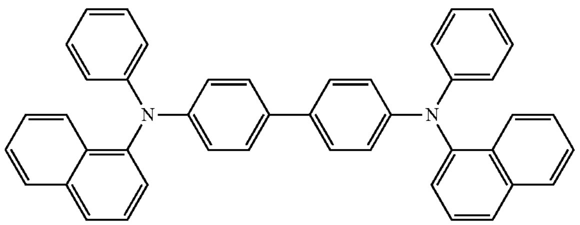

A thickness of the hole transport layer 14 may be about 50 Å to about 1000 Å, for example, about 100 Å to about 800 Å. When the thickness of the hole transport layer 14 is in these ranges, satisfactory hole transport characteristics may be obtained without a substantial increase in driving voltage.

Instead of the hole injection layer 13 and the hole transport layer 14, a functional layer (not illustrated) simultaneously having hole injection and hole transport functions may be formed. A material for forming the functional layer having both hole injection and hole transport functions may be selected from known materials.

At least one of the hole injection layer 13, the hole transport layer 14, and the functional layer simultaneously having hole injection and hole transport functions may further include a charge-generation material for improving the conductivity of the layer, in addition to the condensed-cyclic compound represented by Formula 1, a known hole injection material, and/or a known hole transport material.

Nonlimiting examples of the charge-generation material include p-dopants. Nonlimiting examples of the p-dopant include quinone derivatives such as tetracyanoquinonedimethan (TCNQ) or 2,3,5,6-tetrafluoro-tetracyano-1,4-benzonquinonedimethane (F4TCNQ); metal oxides such as tungsten oxides or molybdenum oxides; and cyano group containing compounds such as hexanitrile hexaazatriphenylene.

When the hole injection layer 13, the hole transport layer 14, or the functional layer simultaneously having hole injection and hole transport functions further includes the charge-generation material, the charge-generation material is homogeneously or non-homogeneously dispersed in the layer.

The emission layer 15 may be formed on the hole transport layer 14 or the functional layer simultaneously having hole injection and hole transport functions by using vacuum deposition, a wet process, or laser transferring. When the emission layer 15 is formed by vacuum deposition or spin coating, the deposition conditions may vary according to the compound used. However, in general, the conditions may be similar to the conditions described above for forming the hole injection layer 13.

The emission layer 15 may include at least one of the condensed-cyclic compound of Formula 1 and a known phosphorescent host, fluorescent host, phosphorescent dopant, or fluorescent dopant. When the emission layer 15 includes the condensed-cyclic compound represented by Formula 1, the condensed-cyclic compound may function as a phosphorescent host, a fluorescent host, a phosphorescent dopant, or a fluorescent dopant.

Nonlimiting examples of known hosts may include 4,4'-N,N'-dicarbazole-biphenyl (CBP), 9,10-di-naphthalene-2-yl-anthracene (AND) (refer to Formula below), TPBI (refer to Formula below), TBADN (refer to Formula below), E3 (refer to Formula below).

ADN

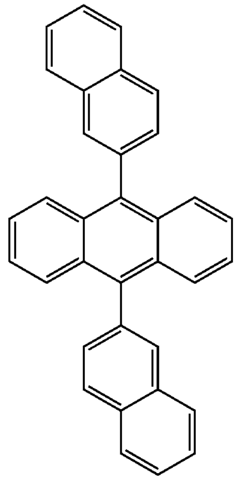

TPBI

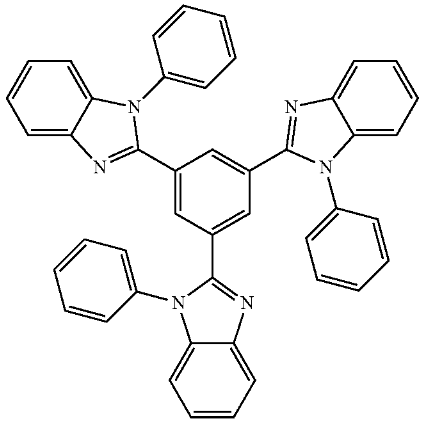

-continued

TBADN

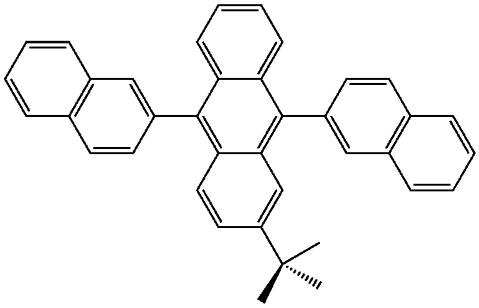

E3

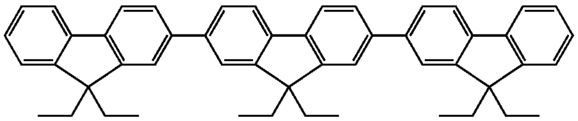

At least one of the fluorescent dopant and the phosphorescent dopant may be used as a dopant. The phosphorescent dopant may be an organic metal complex including Ir, Pt, Os, Re, Ti, Zr, Hf, or combinations including at least two of Ir, Pt, Os, Re, Ti, Zr, and Hf. However, the present invention is not limited thereto.

As a red dopant, PtOEP (refer to Formula below), $Ir(piq)_3$ (refer to Formula below), or $Btp_2Ir(acac)$ (refer to Formula below) may be used. However, the present invention is not limited thereto.

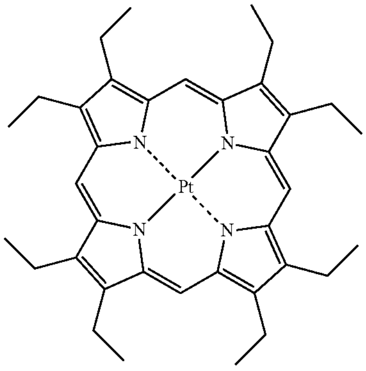

PtOEp

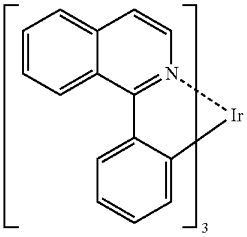

$Ir(piq)_3$

-continued

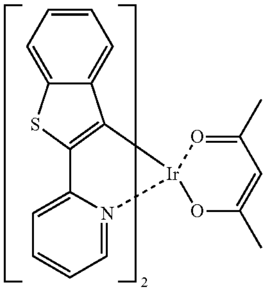

$Btp_2Ir(acac)$

As a green dopant, $Ir(ppy)_3$(ppy=phenyl-pyridines, refer to Formula below), $Ir(ppy)_2(acac)$ (refer to Formula below), or $Ir(mpyp)_3$ (refer to Formula below) may be used. However, the present invention is not limited thereto.

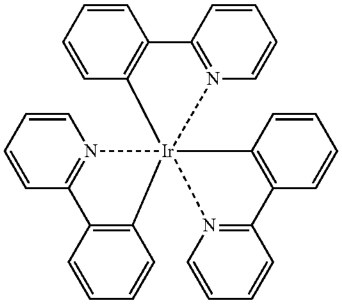

$Ir(ppy)_3$

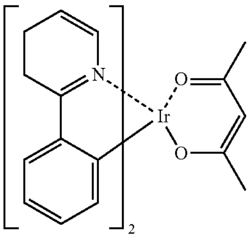

$Ir(ppy)_2(acac)$

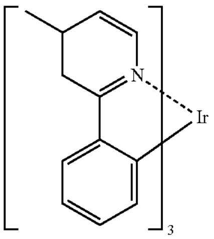

$Ir(mpyp)_3$

As a blue dopant, $F_2Irpic$ (refer to Formula below), $(F_2ppy)_2Ir(tmd)$ (refer to Formula below), $Ir(dfppz)_3$ (refer to Formula below), DPVBi (refer to Formula below), 4,4'-bis(4-diphenylaminosteril)biphenyl (DPAVBi, refer to Formula below), or 2,5,8,11-tetra-tert-butylpherylene (TBPe) (refer to Formula below) may be used. However, the present invention is not limited thereto.

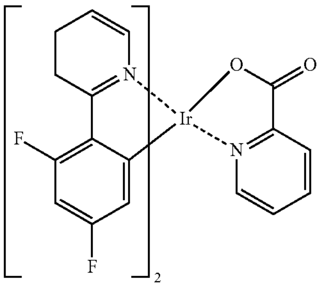

$F_2Irpic$

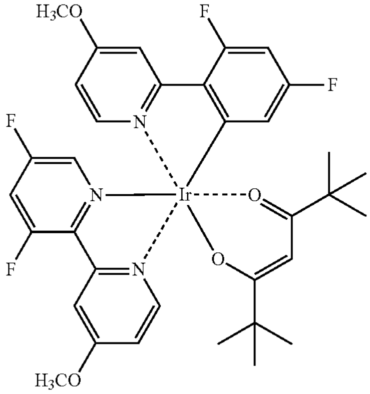

$(F_2ppy)_2Ir(tmd)$

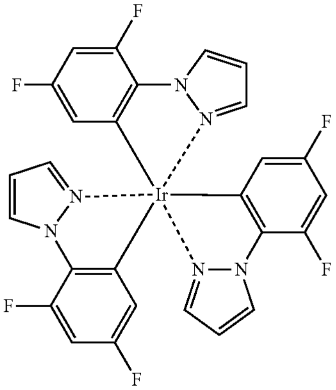

$Ir(dfppz)_3$

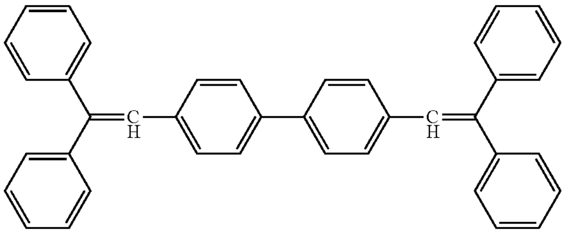

DPVBi

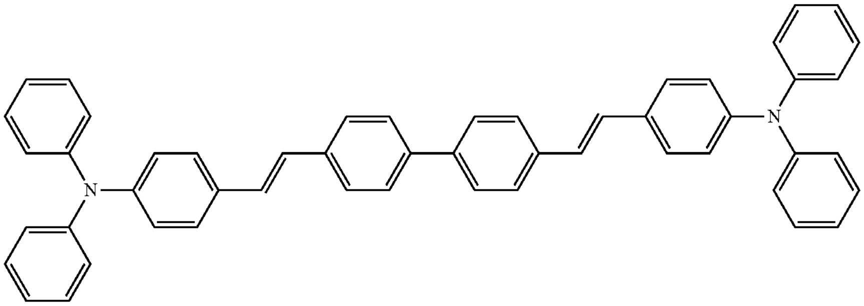

DPAVBi

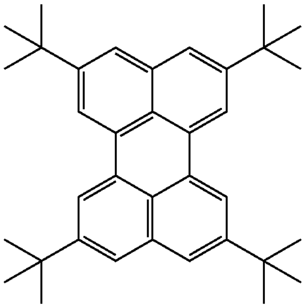

TBPe

When the emission layer 15 includes a host and a dopant, an amount of the dopant may be generally in the range of about 0.01 to about 15 parts by weight based on 100 parts by weight of the host. However, the present invention is not limited thereto.

A thickness of the emission layer 15 may be about 100 Å to about 1000 Å, for example, about 200 Å to about 600 Å. When the thickness of the emission layer 15 is in these ranges, good emission characteristics may be obtained without a substantial increase in driving voltage.

When the phosphorescent dopant is included in the emission layer 15, a hole blocking layer (not illustrated) may be formed between the emission layer 15 and the hole transport layer 16 by vacuum deposition, a wet process, or laser transferring so as to prevent triplet excitons or holes from being diffused to the electron transport layer 16. When the hole blocking layer is formed by vacuum deposition or spin coating, the conditions thereof may vary according to the compound used. However, in general, the conditions may be similar to the conditions described above for forming the hole injection layer 13. Any known hole blocking material may be used. Nonlimiting examples of known hole blocking materials include oxadiazole derivatives, triazole derivatives, and phenanthroline derivatives.

A thickness of the hole blocking layer may be about 50 Å to about 1000 Å, for example, about 100 Å to about 300 Å. When the thickness of the hole blocking layer is in these ranges, good hole blocking characteristics may be obtained without a substantial increase in driving voltage.

The electron transport layer 16 my be formed by vacuum deposition, a wet process, or laser transferring. When the electron transport layer 16 is formed by vacuum deposition or spin coating, the conditions thereof may vary according to the compound used. However, in general, the conditions may be similar to the conditions described above for forming the hole injection layer 13. The condensed-cyclic compound represented by Formula 1 may be used as a material for forming the electron transport layer 16. Also, the electron transport layer 16 may further include a known electron transport material to stably transport electrons injected from the cathode. Nonlimiting examples of known transport materials include quinoline derivatives, in particular, tris(8-quinolinolate)aluminum ($Alq_3$), TAZ (refer to Formula below), Balq (refer to Formula below), beryllium bis benzoquinolin-10-olate ($Bebq_2$). However, the present invention is not limited thereto.

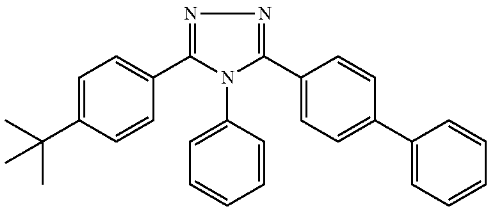

TAZ

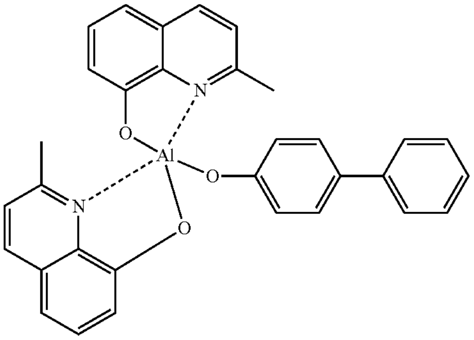

BAlq

A thickness of the electron transport layer 16 may be about 100 Å to about 1000 Å, for example, about 150 Å to about 500 Å. When the thickness of the electron transport layer 16 is in these ranges, good electron transport characteristics may be obtained without a substantial increase in driving voltage.

Also, the electron transport layer 16 may include an organic electron transport compound and a metal-containing material. Nonlimiting examples of the organic electron transport compound include 9,10-di(naphthalene-2-yl)anthracene (AND); and anthracene-based compounds such as a compound 301 or 302 below:

Compound 301

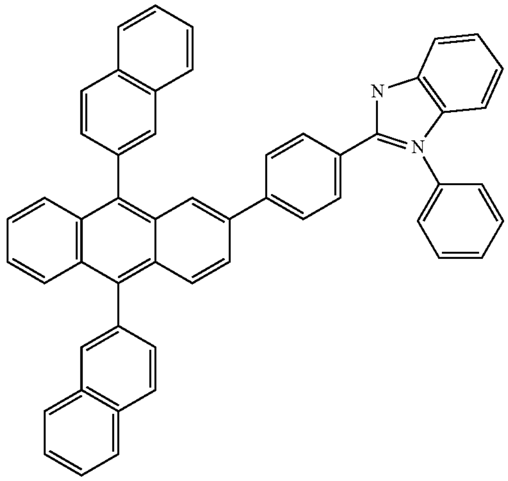

Compound 302

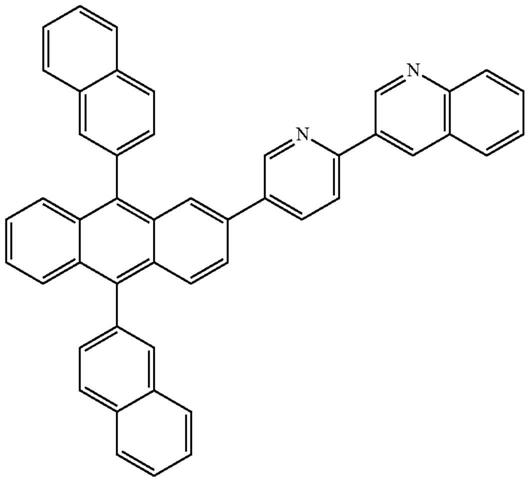

The metal-containing material may include a Li complex. Nonlimiting examples of the Li complex include lithium quinolate (LiQ) or compound 303 below:

Compound 303

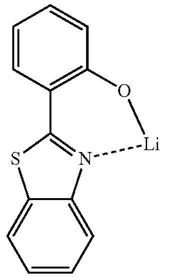

Also, the electron injection layer 17, which facilitates electron injection from a cathode, may be formed on the electron transport layer 16. A material for forming the electron injection layer 17 may include any known material for forming an electron injection layer, such as LiF, NaCl, CsF, $Li_2O$, or BaO. The deposition conditions of the electron injection layer 17 may vary according the compound used. However, in general, the conditions may be similar to the conditions described above for forming the hole injection layer 13.

A thickness of the electron injection layer 17 may be about 1 Å to about 100 Å, for example, about 3 Å to about 90 Å. When the thickness of the electron injection layer 17 is in these ranges, satisfactory hole injection characteristics may be obtained without a substantial increase in driving voltage.

The second electrode 18 may be a transparent electrode and may be formed on the electron injection layer 17. The second electrode 18 may be a cathode, which is an electrode injection electrode. Here, a metal for forming the second electrode 18 may include a metal having a low work function, an alloy, an electric conducting compound, and mixtures thereof. More specifically, the transparent electrode may be a thin film of lithium (Li), magnesium (Mg), aluminum (Al), aluminum-lithium (Al—Li), calcium (Ca), magnesium-indium (Mg—In), or magnesium-silver (Mg—Ag). In order to obtain a top-emission light-emitting device, the transparent electrode may be formed of ITO or IZO.

The organic light-emitting device may be used in a flat panel display apparatus including a transistor.

According to an embodiment of the present invention, a flat panel display apparatus includes an organic light-emitting device including a transistor including a source electrode, a drain electrode, a gate, and an active layer, and an organic layer including the condensed-cyclic compound represented by Formula 1 above. In the organic light-emitting device, the first electrode is electrically connected to the source electrode or the drain electrode. The active layer of the transistor may vary and may be, for example, an amorphous silicon layer, a crystallized silicon layer, an organic semiconductor layer, or an oxide semiconductor layer.

Hereinafter, an organic light-emitting device according to the present invention will be described more specifically with reference to the following Synthesis Examples and Examples. The following Synthesis Examples and Examples are presented for illustrative purposes only and are not intended to limit the scope of the invention.

EXAMPLES

Synthesis Example 1

Synthesis of Compound 1

Compound 1 was synthesized according to Reaction Formula 1 below:

Reaction Formula 1

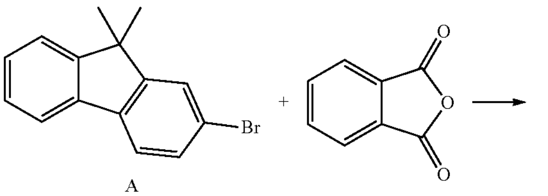

A

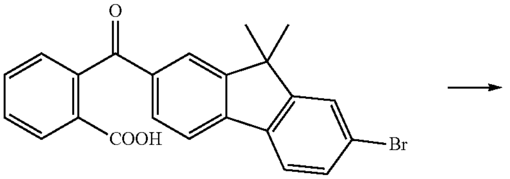

B

-continued

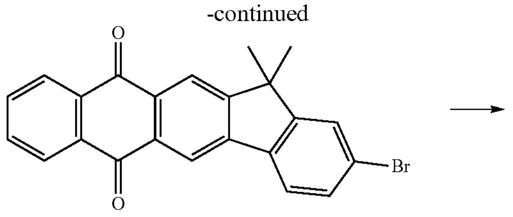

C

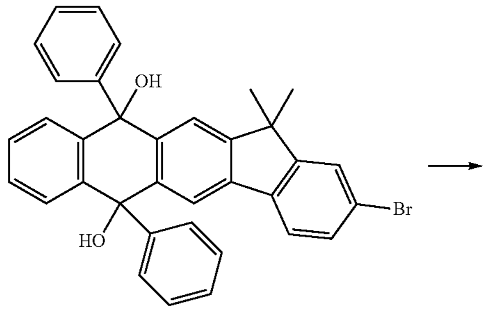

D

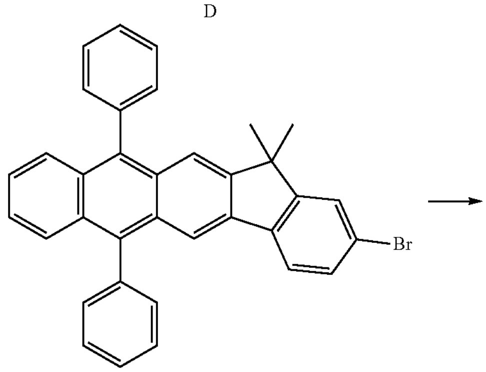

E

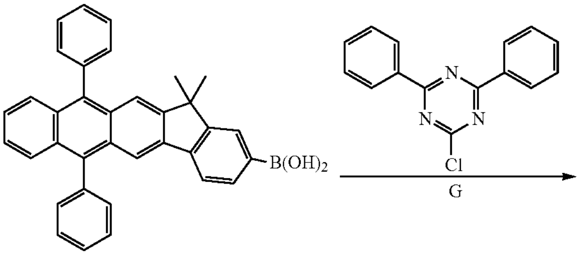

F

Compound 1

1) Synthesis of Intermediate B 27.3 g (0.1 mol) of intermediate A and 16.3 g (0.11 mol) of phthalic anhydride were put in a flask and dichloromethane was added to the flask. 20 g (0.15 mol) of aluminum chloride was gradually added to the flask at 0° C. and then was stirred for 12 hours at room temperature so as to obtain a reaction mixture. After the reaction was completed, distilled water was slowly added to the reaction mixture and the mixture was extracted using dichloromethane. Then, the solvent was removed and a solid was obtained. The obtained solid was washed using hexane, filtered, and dried, thereby obtaining 33.7 g (yield 80%) of intermediate B. 1H-NMR (400 MHz, CDCl3) 8.23 (1H), 7.99 (1H), 7.93 (2H), 7.83 (1H), 7.75 (3H), 7.66 (1H), 7.53 (1H), 1.67 (6H)

2) Synthesis of Intermediate C 33.7 g (80.0 mmol) of intermediate B was put in a flask and polyphosphoric acid was added to the flask. Then, the flask was stirred for 2 hours at 130° C. so as to obtain a mixture. The mixture was cooled down to room temperature and distilled water was gradually added to the mixture, thereby obtaining a solid. The obtained solid was filtered and washed using a small amount of methanol, thereby obtaining 26.8 g (yield 83%) of intermediate C. 1H-NMR (400 MHz, CDCl3) 8.84 (1H), 8.12 (1H), 7.78-7.75 (4H), 7.56 (3H), 1.67 (6H)

3) Synthesis of Intermediate E 10 g (24.8 mmol) of intermediate C was put in 250 ml of THF, which was dried under a nitrogen atmosphere, so as to obtain a mixture. Then, the temperature was lowered to −78° C. and then 50.0 mL (0.5 M) of 2-naphthylmagnesiumbromide was slowly added to the mixture so as to obtain a reaction mixture. The temperature was increased to room temperature and then the reaction mixture was stirred for 3 hours. An ammonium chloride aqueous solution was added to the reaction mixture and the mixture was then extracted using dichloromethane, thereby obtaining an organic layer. The organic layer was dried using anhydrous magnesium sulfate and the solvent was removed so as to obtain a mixture. The mixture was dissolved using a small amount of ethyl ether, petroleum ether was added to the mixture, and the mixture was stirred for a few hours, thereby obtaining a solid compound. The solid compound was vacuum dried and a solid product was obtained. Then, in a nitrogen atmosphere, the solid product was dispersed in 200 ml of acetic acid so as to form a mixture. Then, 41 g (250 mmol) of potassium iodide and 44 g (500 mmol) of sodium hypophosphate hydrate were added to the mixture and then stirred and refluxed for 3 hours so as to form a reaction mixture. After the reaction was completed, an excessive amount of distilled water was added to the reaction mixture so as to form a solid. Then, the solid was filtered, washed using water and methanol, and vacuum dried, thereby obtaining 11.3 g of light-yellow intermediate E (yield 73%). 1H-NMR (400 MHz, CDCl3) 8.10 (1H), 7.95 (1H), 7.91 (2H), 7.70 (2H), 7.73-7.78 (4H), 7.66-7.61 (5H), 7.51 (2H), 7.35 (4H), 7.26 (2H), 1.67 (6H)

4) Synthesis of Intermediate F 6.3 g (10 mmol) of intermediate E was dissolved in 70 ml of THF, which was dried under a nitrogen atmosphere, so as to obtain a mixture. Then, 4.8 ml (2.5 M) of butyllithium was added to the mixture at −78° C. so as to form a mixture solution. The mixture solution was stirred for 1 hour at the same temperature and 1.7 ml (15 mmol) of trimethyl borate was added to the mixture solution. The temperature was increased to room temperature. After 1 hour, 2 N aqueous hydrochloric acid was added to the mixture solution and was stirred for 3 hours, thereby obtaining a solid compound. The obtained solid compound was washed using toluene and filtered, thereby obtaining 4.7 g of light-yellow intermediate F (yield 81%).

5) Synthesis of Intermediate G 20 g (108.5 mmol) of 2,4,6-trichloro-1,3,5-triazine was dissolved in 50 ml of anhydrous tetrahydrofuran, so as to obtain a mixture. Then, 228 mL (227.8 mmol) of 1M phenylmagnesiumbromide was gradually added to the mixture at 0° C., so as to obtain a mixture solution. The temperature was increased to room temperature and the mixture solution was stirred for 4 hours. The remaining grignard reagent was removed using 200 ml of an aqueous ammonium chloride solution, the mixture solution was neutralized using 300 ml of an aqueous sodium hydrogen carbonate solution, and then extracted using 3×50 mL of tetrahydrofuran. Moisture was removed using anhydrous magnesium sulfate, the resulting solid was filtered, and excess solvent was removed using vacuum distillation and the solid was recrystallized using hexane, thereby obtaining 15 g of the compound of Formula G (52%)(MS: [M+H]=268).

6) Synthesis of Compound 1

3.2 g (8.0 mmol) of the compound of Intermediate F and 1.7 g (6.3 mmol) of the compound of Intermediate G were completely dissolved in 100 ml of tetrahydrofuran, so as to obtain a mixture. Then, a 2M aqueous potassium carbonate solution was added to the mixture and then, 155 mg (0.013 mmol) of tetrakis(triphenylphosphine)palladium was added to the mixture, thereby heating and stirring for 5 hours to obtain a mixture solution. The temperature was lowered to room temperature, a material layer of the mixture solution was removed, the mixture solution was dried using anhydrous magnesium sulfate, was vacuum evaporated, and was slowly separated using column chromatography (tetrahydrofuran: hexane=1:6), thereby obtaining 1.5 g of compound 1 (36%) (MS: [M+H]=677).

Synthesis Example 2

Synthesis of Compound 4

Compound 4 was obtained in the same manner as in the Synthesis Example of Compound 1, except that 50.0 ml of 0.5 M 2-phenylmagnesiumbromide was used instead of 50.0 ml of 0.5 M 2-naphthylmagnesiumbromide when synthesizing intermediate E (MS: [M+H]=778).

Synthesis Example 3

Synthesis of Compound 15

Compound 15 was synthesized according to Reaction Formula 2 below:

Reaction Formula 2

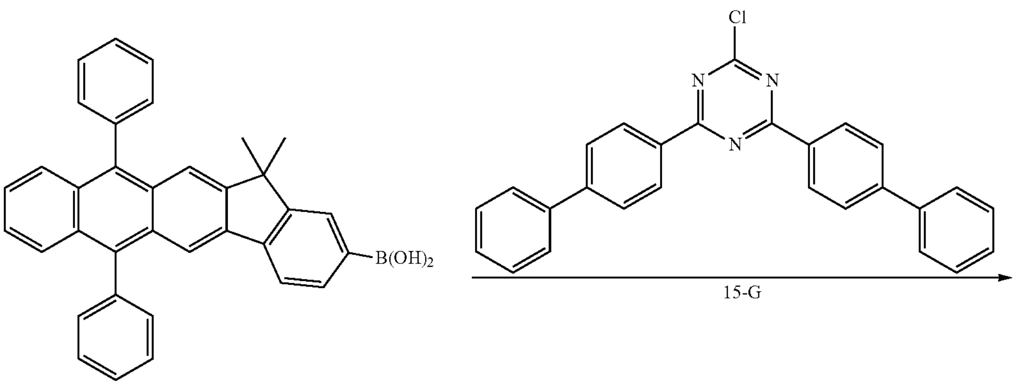

Compound 15

F

Synthesis of Intermediate 15-G 20 g (108.5 mmol) of 2,4,6-trichloro-1,3,5-triazine was dissolved in 50 ml of anhydrous tetrahydrofuran, so as to obtain a mixture. Then, 228 mL (227.8 mmol) of 1M biphenylmagnesiumbromide was gradually added to the mixture at 0° C., so as to obtain a mixture solution. The temperature was increased to room temperature and the mixture solution was stirred for 4 hours. The remaining grignard reagent was removed using 200 ml of an aqueous ammonium chloride solution, the mixture solution was neutralized using 300 ml of an aqueous sodium hydrogen carbonate solution, and then extracted using 3×50 mL of tetrahydrofuran. Moisture was removed using anhydrous magnesium sulfate and the solid was filtered, and excess solvent was removed using vacuum distillation and the solid was recrystallized using hexane, thereby obtaining 16.5 g of the compound in Formula 15-G (53%) (MS: [M+H]=420).

Synthesis of Compound 15

3.2 g (8.0 mmol) of the compound of Intermediate F and 1.7 g (6.3 mmol) of the compound of Intermediate 15-G were completely dissolved in 100 ml of tetrahydrofuran, so as to obtain a mixture. Then, a 2M aqueous potassium carbonate solution was added to the mixture and then, 155 mg (0.013 mmol) of tetrakis(triphenylphosphine)palladium was added to the mixture, and the mixture was heated and stirred for 5 hours to obtain a mixture solution. The temperature was lowered to room temperature, the material layer of the mixture solution was removed, the mixture solution was dried using anhydrous magnesium sulfate, vacuum evaporated, and slowly separated using column chromatography (tetrahydrofuran:hexane=1:7), thereby obtaining 15 g of compound 15 (36%) (MS: [M+H]=930).

Synthesis Example 4

Synthesis of Compound 17

Compound 17 was synthesized according to Reaction Formula 3 below:

Synthesis of Intermediate 17-G 20 g (108.5 mmol) of 2,4,6-trichloro-1,3,5-triazine was dissolved in 50 ml of anhydrous tetrahydrofuran, so as to obtain a mixture. Then, 233 mL (227.8 mmol) of 1M 2-naphthylmagnesiumbromide was gradually added to the mixture at 0° C., so as to obtain a mixture solution. The temperature was increased to room temperature and the mixture solution was stirred for 5 hours. The remaining grignard reagent was removed using 200 ml of an aqueous ammonium chloride solution, the mixture was neutralized using 300 ml of an aqueous sodium hydrogen carbonate solution, and then extracted using 3×50 mL of tetrahydrofuran. Moisture was removed using anhydrous magnesium sulfate and the solid was filtered, and excess solvent was removed using vacuum distillation and the solid was recrystallized using hexane, thereby obtaining 15.2 g of the compound in Formula 17-G (49%)(MS: [M+H]=368).

Synthesis of Compound 17

3.2 g (8.0 mmol) of the compound of Intermediate F and 1.7 g (6.3 mmol) of the compound of Intermediate 17-G were completely dissolved in 100 ml of tetrahydrofuran, so as to obtain a mixture. Then, a 2M aqueous potassium carbonate solution was added to the mixture and then, 155 mg (0.013 mmol) of tetrakis(triphenylphosphine)palladium was added to the mixture, and the mixture was heated and stirred for 5 hours to obtain a mixture solution. The temperature was lowered to room temperature, the material layer of the mixture solution was removed, the mixture solution was dried using anhydrous magnesium sulfate, vacuum evaporated, and slowly separated using column chromatography (tetrahydrofuran:hexane=1:5), thereby obtaining 1.0 g of compound 17 (31%) (MS: [M+H]=778).

Reaction Formula 3

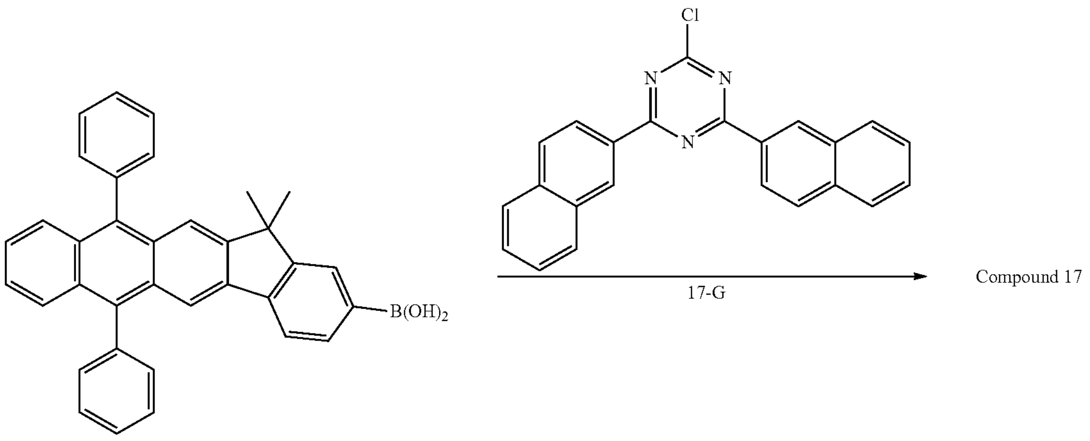

F

Synthesis Example 5

Synthesis of Compound 25

Compound 25 was synthesized according to Reaction Formula 4 below:

Reaction Formula 4

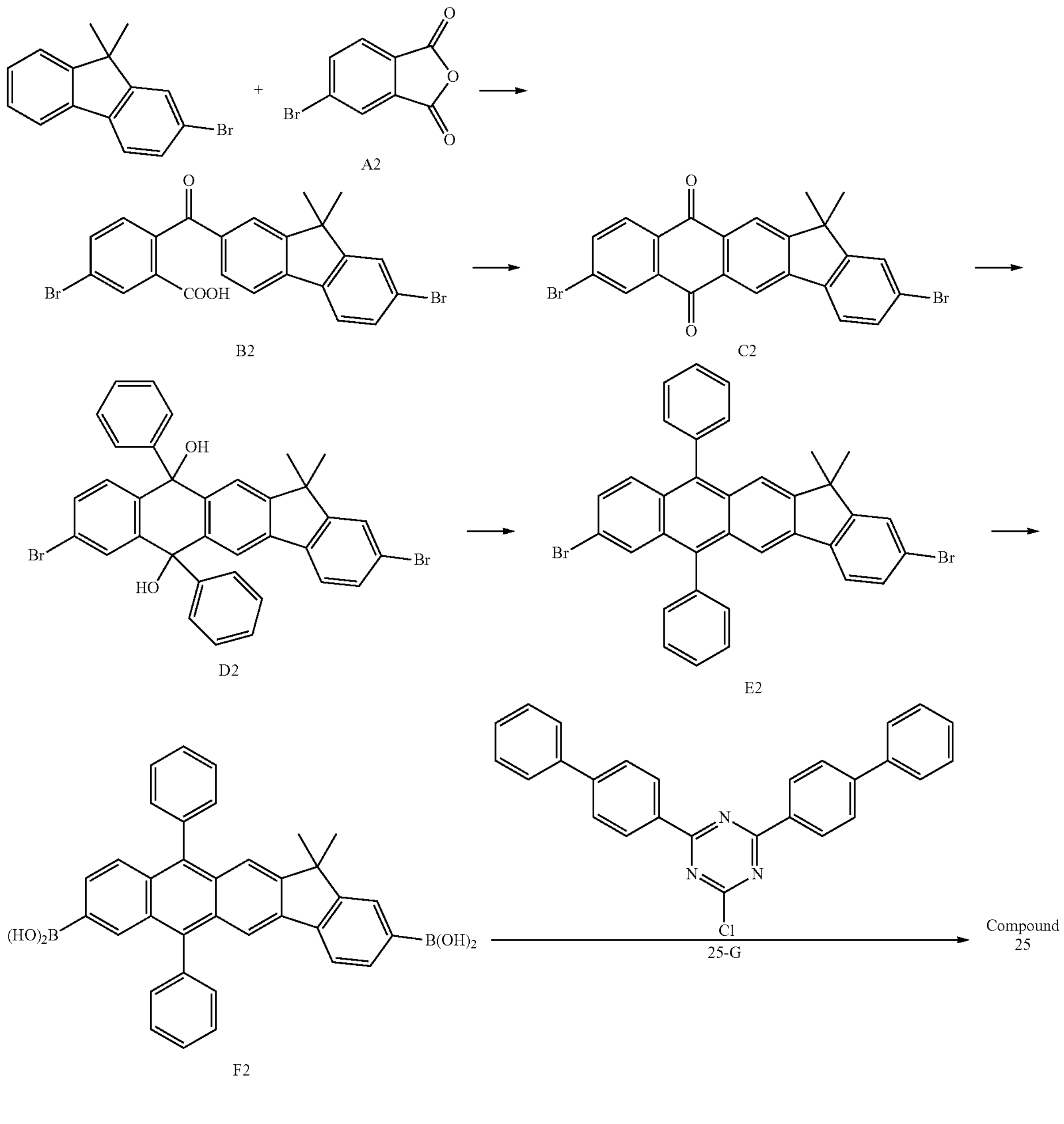

Synthesis of Intermediate B2

27.3 g (0.1 mol) of 2-bromo dimethyl fluorene and 16.3 g (0.11 mol) of 2-bromo-phthalic anhydride were put in a flask and dichloromethane was added to the flask. 20 g (0.15 mol) of aluminum chloride was gradually added to the flask at 0° C. and then was stirred for 12 hours at room temperature so as to obtain a reaction mixture. After the reaction was completed, distilled water was slowly added to the reaction mixture and the mixture was extracted using dichloromethane. Then, the solvent was removed and a solid was obtained. The obtained solid was washed using hexane, filtered, and dried, thereby obtaining 29.6 g (yield 77%) of intermediate B2. 1H-NMR (400 MHz, CDCl3) 8.23 (1H), 7.99 (1H), 7.93 (2H), 7.83 (1H), 7.75 (3H), 7.66 (1H), 7.53 (1H), 1.67 (6H)

Synthesis of Intermediate C2

29.6 g (80.0 mmol) of intermediate B2 was put in a flask and polyphosphate was added to the flask. Then, the flask was stirred for 2 hours at 130° C. so as to obtain a mixture. The mixture was cooled down to room temperature and distilled water was gradually added to the mixture, thereby obtaining a solid. The obtained solid was filtered and washed using a small amount of methanol, thereby obtaining 25.6 g (yield 81%) of intermediate C2. 1H-NMR (400 MHz, CDCl3) 8.84 (1H), 8.12 (1H), 7.78-7.75 (4H), 7.56 (3H), 1.67 (6H)

Synthesis of Intermediate E2

10 g (24.8 mmol) of intermediate C was put in 250 ml of THF, which was dried under a nitrogen atmosphere, so as to obtain a mixture. Then, the temperature was lowered to −78° C. and then 50.0 mL (0.5 M) of 2-naphthylmagnesiumbromide was slowly added to the mixture so as to obtain a reaction mixture. The temperature was increased to room temperature and then the reaction mixture was stirred for 3 hours. An ammonium chloride aqueous solution was added to the reaction mixture and the mixture was then extracted using dichloromethane, thereby obtaining an organic layer. The organic layer was dried using anhydrous magnesium sulfate and the solvent was removed so as to obtain a mixture. The mixture was dissolved using a small amount of ethyl ether, petroleum ether was added to the mixture, and the mixture was stirred for a few hours, thereby obtaining a solid compound. The solid compound was vacuum dried and a solid product was obtained. Then, in a nitrogen atmosphere, the solid product was dispersed in 200 ml of acetic acid so as to form a mixture. Then, 41 g (250 mmol) of potassium iodide and 44 g (500 mmol) of sodium hypophosphate hydrate were added to the mixture and then stirred and refluxed for 3 hours so as to form a reaction mixture. After the reaction was completed, an excess amount of distilled water was added to the reaction mixture so as to form a solid. Then, the solid was filtered, washed using water and methanol, and vacuum dried, thereby obtaining 11.3 g of light-yellow intermediate E (yield 73%). 1H-NMR (400 MHz, CDCl3) 8.10 (1H), 7.95 (1H), 7.91 (2H), 7.70 (2H), 7.73-7.78 (4H), 7.66-7.61 (5H), 7.51 (2H), 7.35 (4H), 7.26 (2H), 1.67 (6H)

Synthesis of Intermediate F2

6.3 g (10 mmol) of intermediate E2 was dissolved in 70 ml of THF, which was dried under a nitrogen atmosphere, so as to obtain a mixture. Then, 7.2 ml (2.5 M) of butyllithium was added to the mixture at −78° C. so as to form a mixture solution. The mixture solution was stirred for 1 hour at the same temperature and 5.0 ml (15 mmol) of trimethyl borate was added to the mixture solution. The temperature was increased to room temperature. After 1 hour, 2 N of aqueous hydrochloric acid was added to the mixture solution and was stirred for 3 hours, thereby obtaining a solid compound. The obtained solid compound was washed using toluene and filtered, thereby obtaining 4.7 g of light-yellow intermediate F (yield 81%).

Synthesis of Intermediate 25-G 20 g (108.5 mmol) of 2,4,6-trichloro-1,3,5-triazine was dissolved in 50 ml of anhydrous tetrahydrofuran, so as to obtain a mixture. Then, 228 mL (227.8 mmol) of 1M biphenylmagnesiumbromide was gradually added to the mixture at 0° C., so as to obtain a mixture solution. The temperature was increased to room temperature and the mixture solution was stirred for 4 hours. The remaining grignard reagent was removed using 200 ml of an aqueous ammonium chloride solution, was neutralized using 300 ml of an aqueous sodium hydrogen carbonate solution, and the mixture solution was then extracted using 3×50 mL of tetrahydrofuran. Moisture was removed using anhydrous magnesium sulfate and the solid was filtered, and excess solvent was removed using vacuum distillation and the solid was recrystallized using hexane, thereby obtaining 17 g of compound in Formula 25-G (52%) (MS: [M+H]=420).

Synthesis of Compound 25

3.2 g (8.0 mmol) of Intermediate F2 and 5.1 g (18.9 mmol) of Intermediate 25-G were completely dissolved in 100 ml of tetrahydrofuran, so as to obtain a mixture. Then, a 2M aqueous potassium carbonate solution was added to the mixture and then, 200 mg (0.018 mmol) of tetrakistriphenylphosphinopaladium was added to the mixture, and the mixture was heated and stirred for 15 hours to obtain a mixture solution. Temperature was lowered to room temperature, the material layer of the mixture solution was removed, the mixture solution was dried using anhydrous magnesium sulfate, vacuum evaporated, and slowly separated using column chromatography once (tetrahydrofuran:hexane=1:3), thereby obtaining 1.5 g of compound 25 (32%) (MS: [M+H]=1214).

Comparative Synthesis Example 1

Synthesis of Compound 201

Compound 201 was manufactured according to Reaction Formula 5 below:

Reaction Formula 5

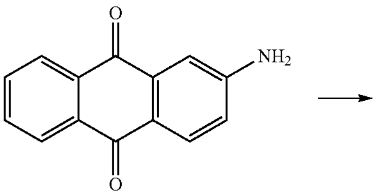

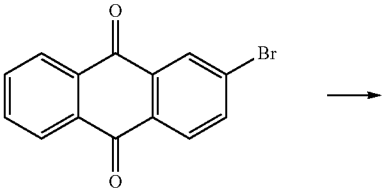

1a

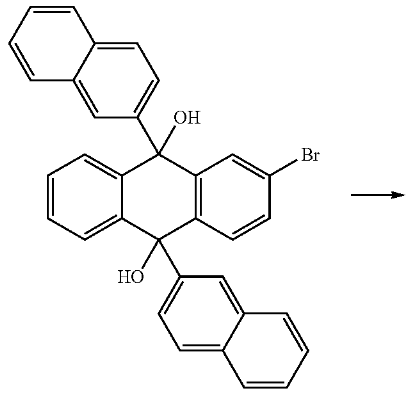

-continued

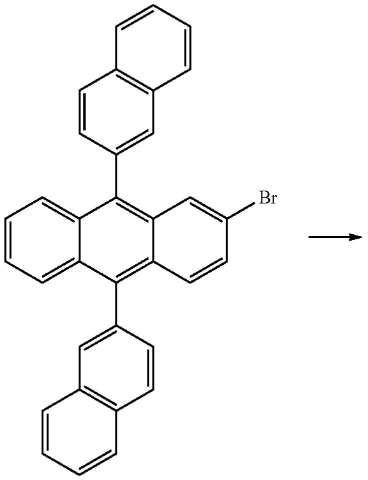

1b

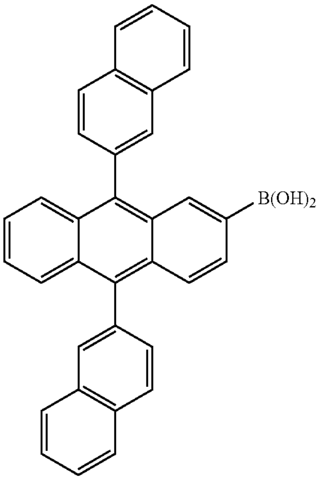

1c

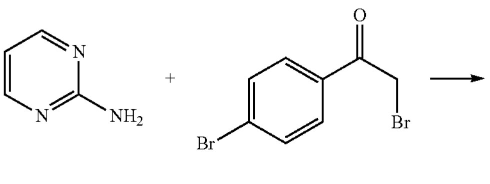

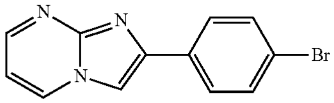

1d

-continued

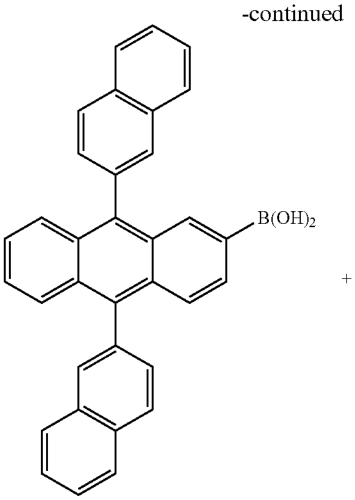

1c

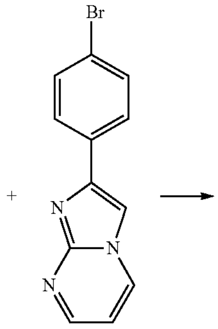

1d

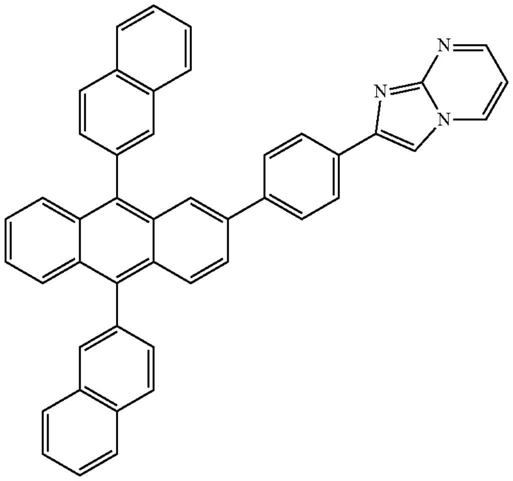

Compound 201

Synthesis of Intermediate 1a 10 g (44 mmol) of copper bromide and 8 g (35.8 mmol) of 2-amino-anthraquinone were put in 250 ml of bromic acid so as to form a mixture. The mixture was heated to 65° C. When gas generation was completed, the mixture was cooled down to room temperature so as to form a reaction solution. The reaction solution was added to 1000 ml of 20% aqueous hydrochloric acid and was extracted using dichloromethane, thereby obtaining an organic layer. The remaining moisture of the organic layer was removed using anhydrous magnesium sulfate and vacuum dried, thereby obtaining a product. The product was separated using column chromatography (dichloromethane:normal hexane=4:1), thereby obtaining 7.7 g of intermediate 1a.

2) Synthesis of Intermediate 1b 10 g (34.8 mmol) of intermediate 1a was put in 100 ml of THF, which was dried under a nitrogen atmosphere, so as to obtain a mixture. Then, the temperature was lowered to −78° C. and then 0.5 M 2-naphthylmagnesiumbromide (10 mmol) was slowly added to the mixture so as to obtain a reaction mixture. The temperature was increased to room temperature and then the reaction mixture was stirred for 3 hours. An ammonium chloride aqueous solution was added to the reaction mixture and the mixture was then extracted using dichloromethane, thereby obtaining an organic layer. The organic layer was dried using anhydrous magnesium sulfate and the solvent was removed so as to obtain a mixture. The mixture was dissolved using a small amount of ethyl ether, petroleum ether was added to the mixture, and the mixture was stirred for a few hours, thereby obtaining a solid compound. The solid compound was filtered and vacuum dried, thereby obtaining 17.6 g of dinaphthyldialcohol.

Then, in a nitrogen atmosphere, 17.6 g (32.4 mmol) of dinaphthyldialcohol was dispersed in 200 ml of acetic acid so as to form a mixture. Then, 53.4 g (330 mmol) of potassium iodide and 58 g (660 mmol) of sodium hypophosphate hydrate were added to the mixture and then stirred and refluxed for 3 hours so as to form a reaction mixture. The mixture was cooled down to room temperature, filtered, and washed using water and methanol, and vacuum dried, thereby obtaining 11.3 g of light-yellow intermediate 1b.

3) Synthesis of Intermediate 1c 5 g (9.81 mmol) of intermediate 1b was dissolved in 70 ml of THF, which was dried under a nitrogen atmosphere, so as to obtain a mixture. Then, 4.7 ml (11.8 mmol) of butyllithium was added to the mixture at −78° C. so as to form a mixture solution. The mixture solution was stirred for 1 hour at the same temperature and 2.20 ml (29.4 mmol) of trimethyl borate was added to the mixture solution. The temperature was increased to room temperature. After 1 hour, 2 N aqueous hydrochloric acid was added to the mixture solution and was stirred for 3 hours, thereby obtaining a solid compound. The obtained solid compound was washed using toluene and filtered, thereby obtaining 3.27 g of light-yellow intermediate 1c (yield 70%).

4) Synthesis of Intermediate 1d 3.39 g (35.98 mmol) of 2-aminopyridine and 10 g (35.98 mmol) of 2,4'-dibromoacetophenone were dissolved in 150 ml of ethanol so as to form a mixture. Then, the mixture was refluxed for 12 hours. When the mixture was cooled down to room temperature, a white solid was generated and was filtered while washing using a saturated $NaHCO_3$ solution, thereby obtaining an organic layer. The remaining moisture of the organic layer was removed using anhydrous magnesium sulfate, and the resultant was vacuum dried, and recrystallized (dichloromethane/normal hexane), thereby obtaining 8.02 g of intermediate 1d having a crystal form of a panel (yield 82%).

5) Synthesis of Compound 201

1.85 g (3.90 mmol) of intermediate 1c and 1 g (3.90 mmol) of intermediate 1d were put in a mixed solvent of 2.7 g (19.5 mmol) of potassium carbonate aqueous solution and THF so as to form a mixture. Then, 225 mg (0.196 mmol) of $Pd(PPh_3)_4$ was put in the mixture while stirring, and the mixture was refluxed for 6 hours so as to form a mixture solution. The mixture solution was cooled down to room temperature and then a solid compound was generated. The solid compound was filtered while washing using water, ethanol, and toluene, thereby obtaining 1.73 g (71%) of compound 201. 1H NMR (400 MHz, CDCl3) 8.51 (1H), 8.40 (1H), 8.12 (1H), 8.06-7.99 (5H), 7.96 (2H), 7.85 (1H), 7.78-7.59 (15H), 7.32 (2H), 6.84 (1H)

Comparative Synthesis Example 2

Synthesis of Compound 202

1.73 g (71%) of compound 202 was obtained in the same manner as in Comparative Synthesis Example 1, except that intermediate 2d below was used instead of intermediate 1d when synthesizing. 1H NMR (400 MHz, $CDCl_3$) 8.13-8.04 (7H), 8.01 (1H), 7.97-7.92 (4H), 7.86-7.82 (2H), 7.75 (2H), 7.71-7.58 (10H), 7.32 (2H), 7.15 (1H), 6.75 (1H)

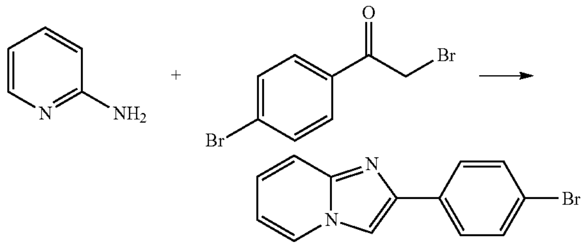

2d

Compound 202

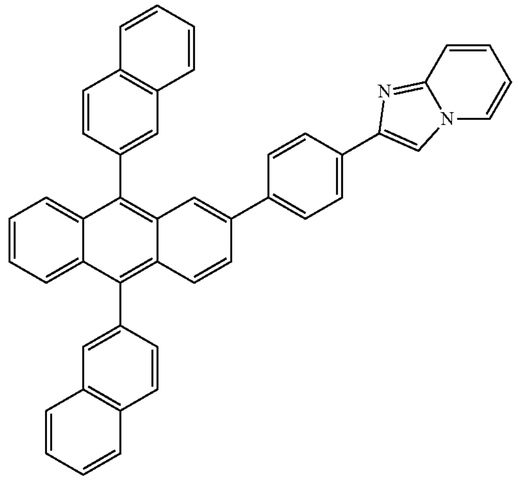

Comparative Synthesis Example 3

Synthesis of Compound 203

Intermediate E-1 was synthesized in the same manner as in Synthesis Example 1, except that a phenyl group was used instead of a naphthyl group when synthesizing intermediate E. 2.05 g (3.90 mmol) of intermediate E-1 and 1.23 g (3.90 mmol) of intermediate H were put in a mixed solvent of 2.7 g (19.5 mmol) of potassium carbonate aqueous solution and toluene so as to form a mixture. Then, 225 mg (0.196 mmol) of $Pd(PPh_3)_4$ was put in the mixture while stirring, and the mixture was refluxed for 6 hours so as to form a mixture solution. The mixture solution was cooled down to room temperature and then a solid compound was generated. The solid compound was filtered while washing using water, ethanol, and toluene, thereby obtaining 1.74 g (70%) of compound 203. $^1$H-NMR (400 MHz, $CDCl_3$) 8.52 (1H), 8.27 (1H), 8.10 (1H), 7.83 (2H), 7.74 (1H), 7.68 (4H), 7.59-7.42 (16H), 7.22 (2H), 1.67 (6H)

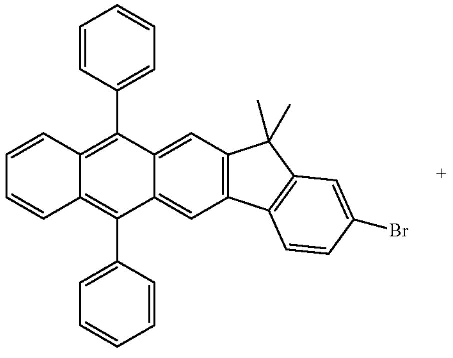

E-1

-continued

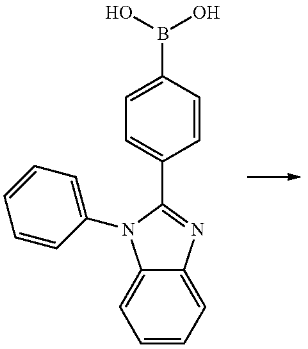

H

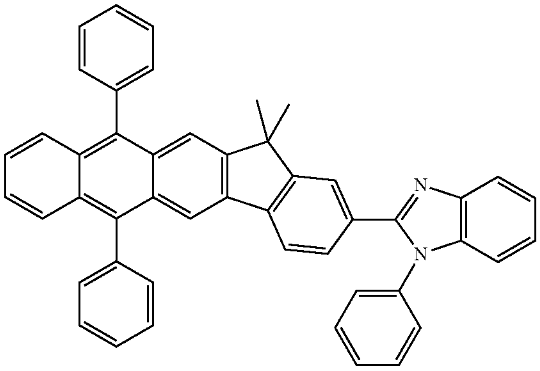

Compound 203

Example 1

As an anode, a 15 Ω/cm² (1200 Å) ITO glass substrate from Corning Co., Ltd. was cut into 50 mm×50 mm×0.7 mm and was ultrasonically washed for 5 minutes each with isopropyl alcohol and purified water. Then, ultraviolet rays were irradiated to the washed ITO glass substrate for 15 minutes and the substrate was washed by exposure to ozone. Then, the ITO glass substrate was deposited in a vacuum deposition device. m-MTDATA was vacuum deposited on the ITO glass substrate so as to form a hole injection layer having a thickness of 600 Å. Then, NPB was vacuum deposited on the hole injection layer, forming a hole transport layer having a thickness of 300 Å. 98% of $Alq_3$, as a green emission host, and 2% of C545T, as a green dopant, were used to form an emission layer having a thickness of 300 Å on the hole transport layer. Compound 1 was vacuum deposited on the emission layer so as to form an electron transport layer having a thickness of 300 Å. LiF was vacuum deposited on the electron transport layer so as to form an electron injection layer having a thickness of 10 Å and then Al was vacuum deposited on the electron injection layer so as to form a cathode having a thickness of 3000 Å. Therefore, an organic light-emitting device was completely manufactured.

Example 2

An organic light-emitting device was manufactured as in Example 1, except that compound 4 was used instead of compound 1 when forming the electron transport layer.

Example 3

An organic light-emitting device was manufactured as in Example 1, except that compound 15 was used instead of compound 1 when forming the electron transport layer.

Example 4

An organic light-emitting device was manufactured as in Example 1, except that compound 17 was used instead of compound 1 when forming the electron transport layer.

Example 5

An organic light-emitting device was manufactured as in Example 1, except that compound 25 was used instead of compound 1 when forming the electron transport layer.

Comparative Example 1

An organic light-emitting device was manufactured as in Example 1, except that $Alq_3$ (aluminum tris(8-hydroxyquinoline)) was used instead of compound 1 when forming the electron transport layer.

Comparative Example 2

An organic light-emitting device was manufactured as in Example 1, except that compound 201 was used instead of compound 1 when forming the electron transport layer.

Comparative Example 3

An organic light-emitting device was manufactured as in Example 1, except that compound 202 was used instead of compound 1 when forming the electron transport layer.

Comparative Example 4

An organic light-emitting device was manufactured as in Example 1, except that compound 203 was used instead of compound 1 when forming the electron transport layer.

Evaluation Example

The organic light-emitting devices of Examples 1 through 5 and the organic light-emitting devices of Comparative Examples 1 through 4 were evaluated in terms of current density, driving voltage, efficiency, color coordinates, and lifetime (T__50%: time used for brightness to reduce below 50%) using PR650 (Spectroscan) Source Measurement Unit (PhotoResearch Co. LTD.). The results are shown in Table 1 below.

TABLE 1

| | Electron transport layer material | Driving voltage (V) | Current density (mA/cm²) | Emission Efficiency (cd/A) | Lifetime (h) | Color Coordinates |
|---|---|---|---|---|---|---|
| Example 1 | Compound 1 | 6.38 | 50 | 15.3 | 75 | (0.309, 0.642) |
| Example 2 | Compound 4 | 6.44 | 50 | 15.8 | 89 | (0.309, 0.641) |
| Example 3 | Compound 15 | 5.81 | 50 | 13.9 | 63 | (0.310, 0.643) |

TABLE 1-continued

| | Electron transport layer material | Driving voltage (V) | Current density (mA/cm$^2$) | Emission Efficiency (cd/A) | Life-time (h) | Color Coordinates |
|---|---|---|---|---|---|---|
| Example 4 | Compound 17 | 5.36 | 50 | 12.5 | 44 | (0.309, 0.641) |
| Example 5 | Compound 25 | 6.74 | 50 | 14.9 | 112 | (0.310, 0.642) |
| Comparative Example 1 | $Alq_3$ | 7.52 | 50 | 11.9 | 38 | (0.309, 0.641) |
| Comparative Example 2 | Compound 201 | 7.23 | 50 | 10.8 | 40 | (0.309, 0.639) |
| Comparative Example 3 | Compound 202 | 7.03 | 50 | 9.7 | 45 | (0.309, 0.640) |
| Comparative Example 4 | Compound 203 | 7.34 | 50 | 10.3 | 29 | (0.309, 0.641) |

According to Table 1, the organic light-emitting devices of Examples 1 through 5 have improved performance, for example, low driving voltages, high emission efficiencies, and long lifetime, as compared to the organic light-emitting devices of Comparative Examples 1 through 4.

The organic light-emitting devices including the condensed-cyclic compound represented by Formula 1 have low driving voltages, high emission efficiencies, and long lifetimes, and thus flat panel display apparatuses have good performance.

While the present invention has been illustrated and described with respect to certain exemplary embodiments, those of ordinary skill in the art will understand that various changes made be made to the described embodiments without departing from the spirit and scope of the present invention as defined by the following claims.

What is claimed is:

1. A condensed-cyclic compound represented by Formula 1;

Formula 1

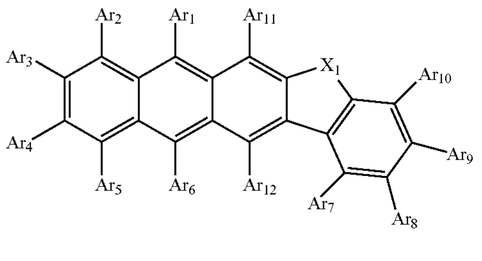

wherein $X_1$ is $CR_1R_2$, $NR_3$, O, or S;

each of $Ar_1$ through $Ar_{12}$ is independently selected from the group consisting of hydrogen atoms, deuterium, halogen atoms, hydroxyl groups, cyano groups, nitro groups, carboxyl groups, substituted $C_1$-$C_{30}$ alkyl groups, unsubstituted $C_1$-$C_{30}$ alkyl groups, substituted $C_2$-$C_{30}$ alkenyl groups, unsubstituted $C_2$-$C_{30}$ alkenyl groups, substituted $C_2$-$C_{30}$ alkynyl groups, unsubstituted $C_2$-$C_{30}$ alkynyl groups, substituted $C_1$-$C_{30}$ alkoxy groups, unsubstituted $C_1$-$C_{30}$ alkoxy groups, substituted $C_3$-$C_{30}$ cycloalkyl groups, unsubstituted $C_3$-$C_{30}$ cycloalkyl groups, substituted $C_3$-$C_{30}$ cycloalkenyl groups, unsubstituted $C_3$-$C_{30}$ cycloalkenyl groups, substituted $C_5$-$C_{30}$ aryl groups, unsubstituted $C_5$-$C_{30}$ aryl groups, substituted $C_5$-$C_{30}$ aryloxy groups, unsubstituted $C_5$-$C_{30}$ aryloxy groups, substituted $C_5$-$C_{30}$ arylthio groups, unsubstituted $C_5$-$C_{30}$ arylthio groups, substituted $C_2$-$C_{30}$ heterocyclic groups, unsubstituted $C_2$-$C_{30}$ heterocyclic groups, groups represented by Formula 2, groups represented by $N(Q_1)(Q_2)$, and groups represented by $Si(Q_3)(Q_4)(Q_5)$;

wherein each of $Q_1$ through $Q_5$ is independently selected from the group consisting of hydrogen atoms, deuterium, halogen atoms, hydroxyl groups, cyano groups, amino groups, nitro groups, carboxyl groups, substituted $C_1$-$C_{30}$alkyl groups, unsubstituted $C_1$-$C_{30}$alkyl groups, substituted $C_2$-$C_{30}$ alkenyl groups, unsubstituted $C_2$-$C_{30}$ alkenyl group, substituted $C_2$-$C_{30}$ alkynyl groups, unsubstituted $C_2$-$C_{30}$ alkynyl groups, substituted $C_1$-$C_{30}$ alkoxy groups, unsubstituted $C_1$-$C_{30}$ alkoxy groups, substituted $C_3$-$C_{30}$ cycloalkyl groups, unsubstituted $C_3$-$C_{30}$ cycloalkyl groups, substituted $C_3$-$C_{30}$ cycloalkenyl groups, unsubstituted $C_3$-$C_{30}$ cycloalkenyl groups, substituted $C_5$-$C_{30}$ aryl groups, unsubstituted $C_5$-$C_{30}$ aryl groups, substituted $C_5$-$C_{30}$ aryloxy groups, unsubstituted $C_5$-$C_{30}$ aryloxy groups, substituted $C_5$-$C_{30}$ arylthio groups, unsubstituted $C_5$-$C_{30}$ arylthio groups, substituted $C_2$-$C_{30}$ heterocyclic groups and unsubstituted $C_2$-$C_{30}$ heterocyclic groups, wherein at least one of $Ar_1$ through $Ar_{12}$ is a group represented by Formula 2;

Formula 2

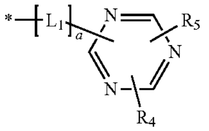

wherein $L_1$ is a substituted or unsubstituted $C_1$-$C_{30}$ alkylene group, a substituted or unsubstituted $C_5$-$C_{30}$ arylene group, or a substituted or unsubstituted divalent $C_2$-$C_{30}$ heterocyclic group;

a is an integer from 0 to 5;

each of $R_1$ through $R_3$ is independently a hydrogen atom, deuterium, a halogen atom, a hydroxyl group, a cyano group, an amino group, a nitro group, a carboxyl group, a substituted or unsubstituted $C_1$-$C_{30}$alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, or a substituted or unsubstituted $C_2$-$C_{30}$ heterocyclic group, and each of $R_4$ and $R_5$ is independently a substituted or unsubstituted $C_1$-$C_{30}$alkyl group, a substituted or unsubstituted $C_2$-$C_{30}$ alkenyl group, a substituted or unsubstituted $C_2$-$C_{30}$ alkenyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, or a substituted or unsubstituted $C_2$-$C_{30}$ heterocyclic group, wherein plural numbers in $R_4$ and $R_5$ are the same as each other or different from each other.

2. The condensed-cyclic compound of claim 1, wherein $X_1$ is $CR_1R_2$.

3. The condensed-cyclic compound of claim 1, wherein $X_1$ is $C(CH_3)(CH_3)$.

4. The condensed-cyclic compound of claim 1, wherein each of $R_1$ through $R_3$ is independently a hydrogen atom, deuterium, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted pyrazolyl group, a substituted or unsubstituted pyridinyl group, a substituted or unsubstituted pyrazinyl group, a substituted or unsubstituted pyrimidinyl group, or a substituted or unsubstituted pyridazinyl group.

5. The condensed-cyclic compound of claim 1, wherein at least one of $Ar_1$, $Ar_3$, $Ar_4$, $Ar_6$, and $Ar_9$ is a group represented by Formula 2.

6. The condensed-cyclic compound of claim 1, wherein each of $Ar_2$, $Ar_5$, $Ar_7$, $Ar_8$, $Ar_{10}$, $Ar_{11}$, and $Ar_{12}$ is a hydrogen atom, and each of $Ar_t$, $Ar_3$, $Ar_4$, $Ar_6$, and $Ar_9$ is independently deuterium, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ aryloxy group, a substituted or unsubstituted $C_5$-$C_{30}$ arylthio group, a substituted or unsubstituted $C_2$-$C_{30}$ heterocyclic group, a group represented by Formula 2 above, a group represented by $N(Q_1)(Q_2)$, or a group represented by $Si(Q_3)(Q_4)(Q_5)$, wherein at least one of $Ar_t$, $Ar_3$, $Ar_4$, $Ar_6$, and $Ar_9$ is a group represented by Formula 2.

7. The condensed-cyclic compound of claim 1, wherein each of $Ar_2$, $Ar_5$, $Ar_7$, $Ar_8$, $Ar_{10}$, $Ar_{11}$, and $Ar_{12}$ is a hydrogen atom, and each of $Ar_1$, $Ar_3$, $Ar_4$, $Ar_6$, and $Ar_9$ is independently a hydrogen atom, deuterium, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazolyl group, a substituted or unsubstituted oxazolyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyl group, a substituted or unsubstituted dibenzothiophenyl group, or a group represented by Formula 2 above, wherein at least one of $Ar_1$, $Ar_3$, $Ar_4$, $Ar_6$, and $Ar_9$ is a group represented by Formula 2.

8. The condensed-cyclic compound of claim 1, wherein $L_1$ in Formula 2 is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenyl group, a substituted or unsubstituted naphthacenyl group, a substituted or unsubstituted picenyl group, a substituted or unsubstituted perylenylene group, a substituted or unsubstituted pentaphenylene group, or a substituted or unsubstituted hexalenylene group.

9. The condensed-cyclic compound of claim 1, wherein a in Formula 2 is 0 or 1.

10. The condensed-cyclic compound of claim 1, wherein each of $R_4$ and $R_5$ in Formula 2 is independently a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted indenoanthracenyl group, a substituted or unsubstituted pyrazolyl group, a substituted or unsubstituted pyridinyl group, a substituted or unsubstituted bipyridinyl group, a substituted or unsubstituted pyridazinyl group, a substituted or unsubstituted pyrimidinyl group, a substituted or unsubstituted pyrazinyl group, a substituted or unsubstituted quinolinyl group, or a substituted or unsubstituted phenanthrolinyl group.

11. The condensed-cyclic compound of claim 1, wherein $R_4$ and $R_5$ are the same as each other and each of $R_4$ and $R_5$ is a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted biphenyl group, a substituted or unsubstituted naphthyl group, a substituted or unsubstituted fluorenyl group, a substituted or unsubstituted spiro-fluorenyl group, a substituted or unsubstituted anthryl group, a substituted or unsubstituted indenoanthracenyl group, a substituted or unsubstituted pyrazolyl group, a substituted or unsubstituted pyridinyl group, a substituted or unsubstituted bipyridinyl group, a substituted or unsubstituted pyridazinyl group, a substituted or unsubstituted pyrimidinyl group, a substituted or unsubstituted pyrazinyl group, a substituted or unsubstituted quinolinyl group, or a substituted or unsubstituted phenanthrolinyl group.

12. The condensed-cyclic compound of claim 1, wherein the group represented by Formula 2 is selected from the group consisting of groups represented by Formulas 2A through 2U:

Formula 2A

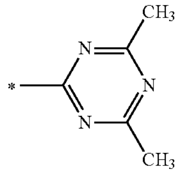

Formula 2B

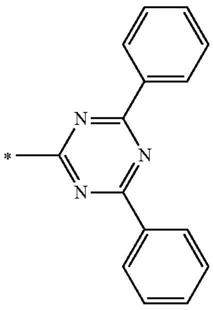

-continued

Formula 2C

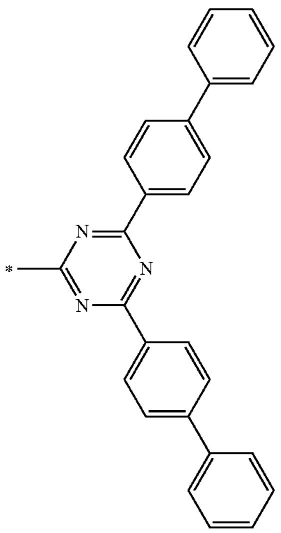

Formula 2D

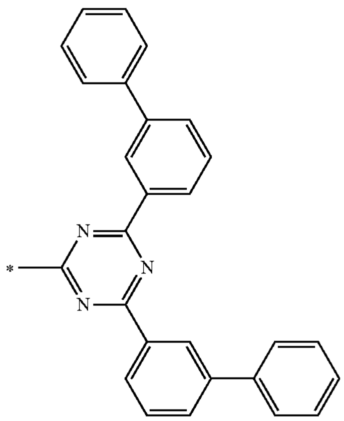

Formula 2E

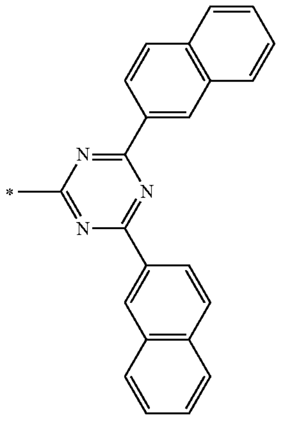

-continued
Formula 2F
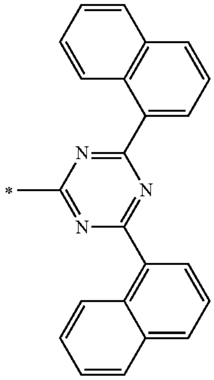
Formula 2G
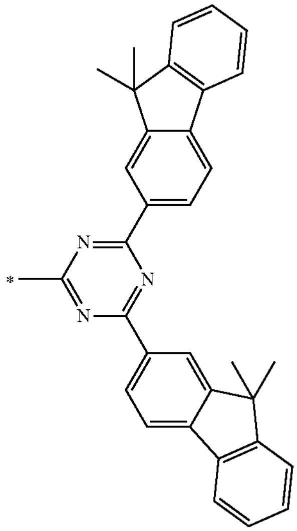
Formula 2H
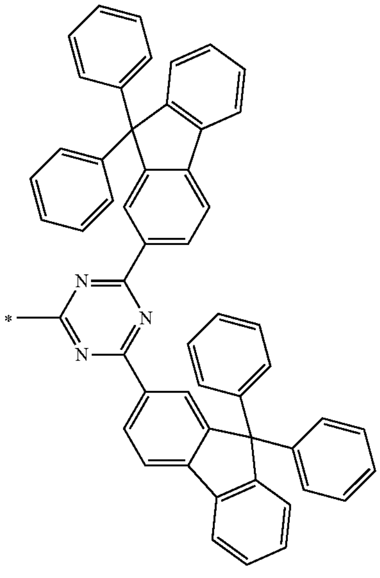
-continued
Formula 2I
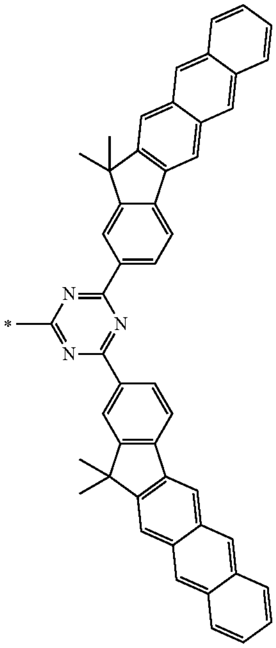
Formula 2J
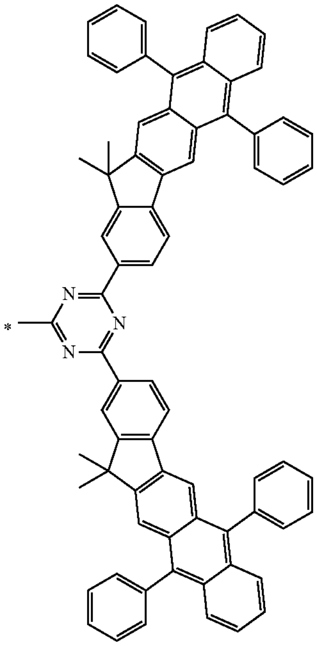
Formula 2K
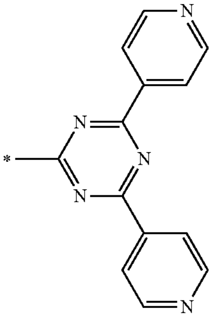

-continued
Formula 2L
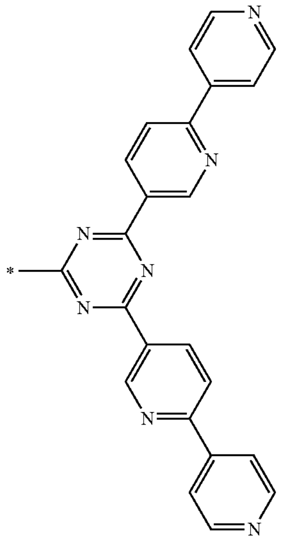
Formula 2M
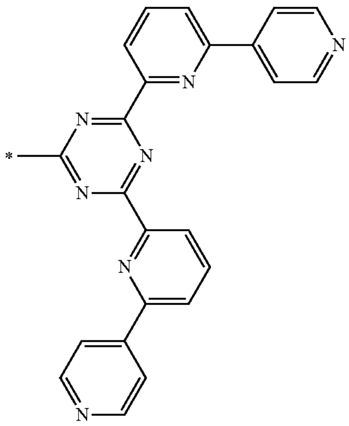
Formula 2N
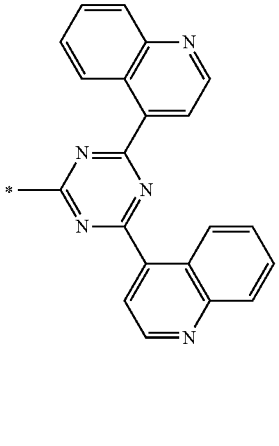
-continued
Formula 2O
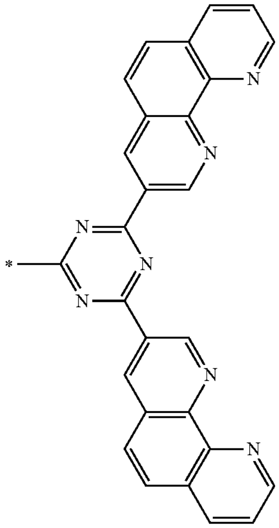
Formula 2P
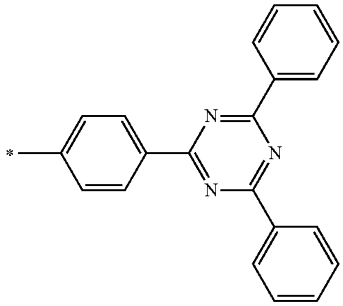
Formula 2Q
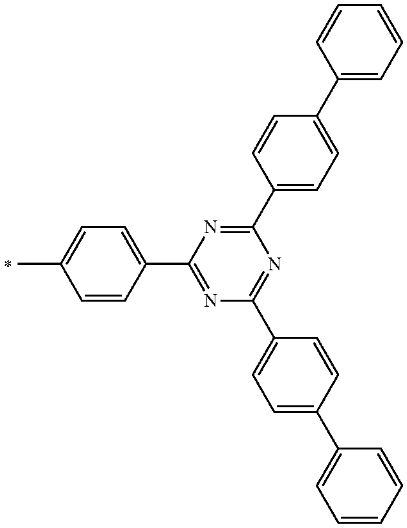

-continued
Formula 2R
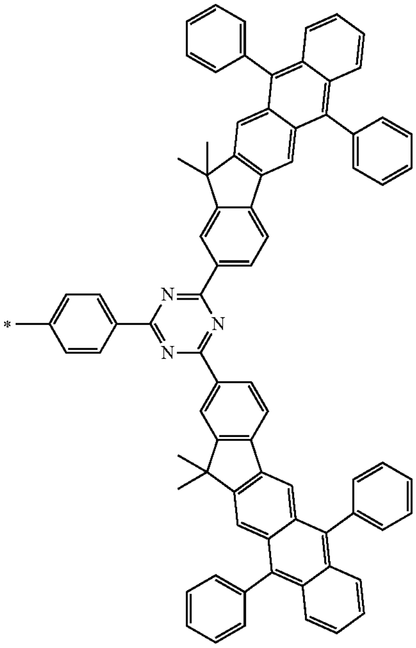
Formula 2S
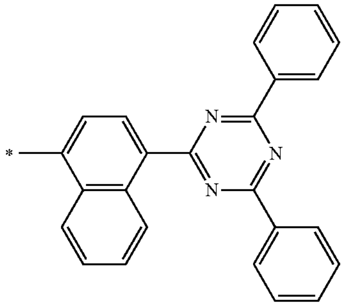
-continued
Formula 2T
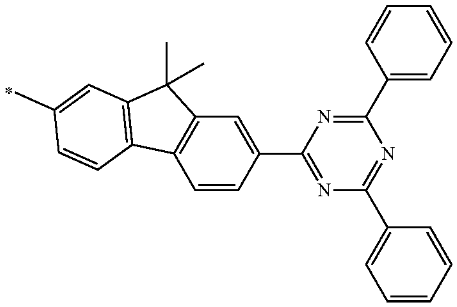
Formula 2U
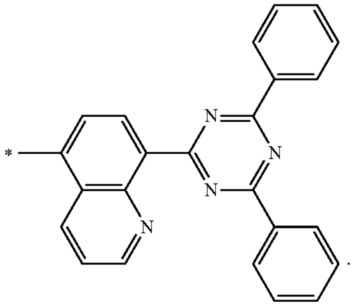
13. The condensed-cyclic compound of claim 1, wherein the condensed-cyclic compound represented by Formula 1 is selected from the group consisting of compounds represented by Compounds 1 through 40:
Compound 1
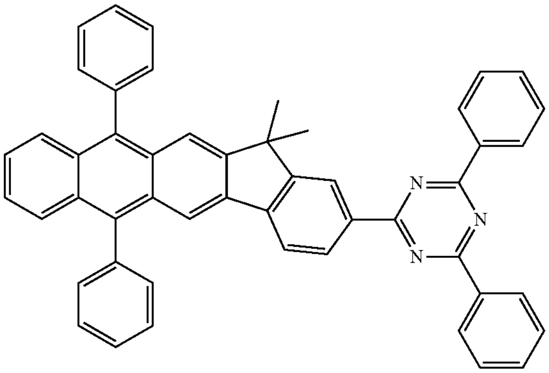
Compound 2
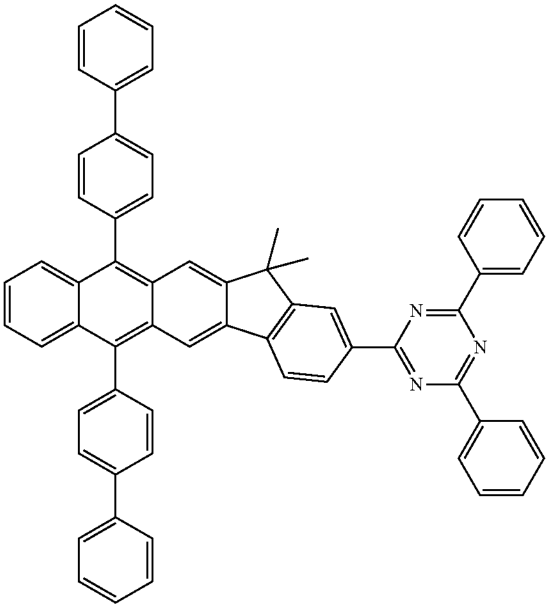

-continued
Compound 3
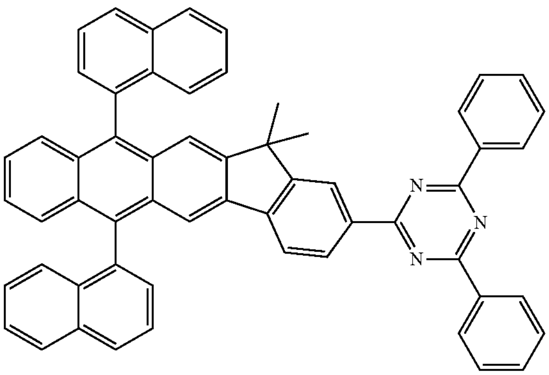
Compound 4
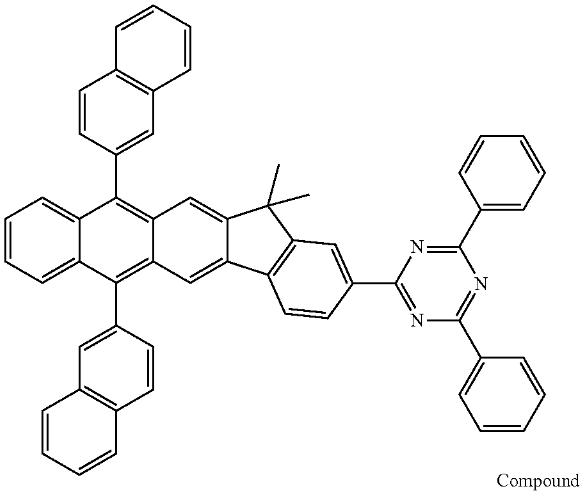
Compound 5
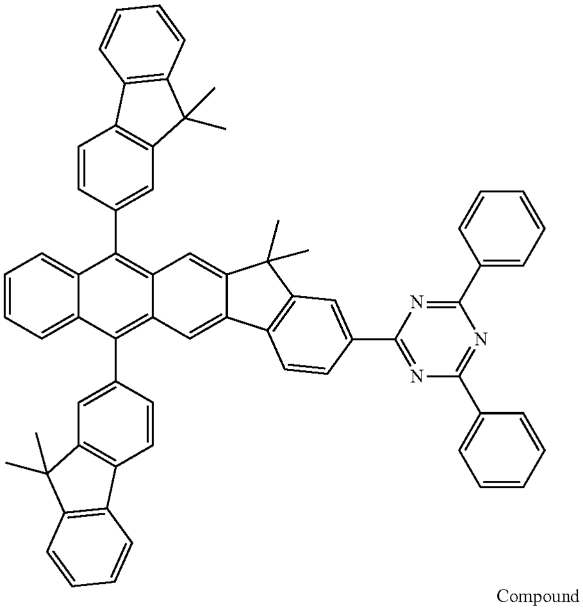
Compound 6
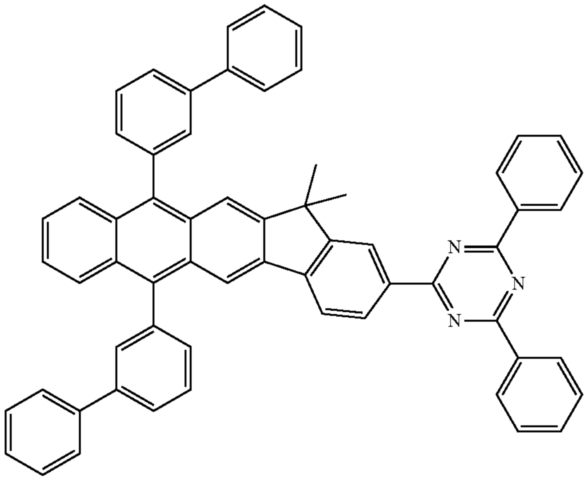
Compound 7
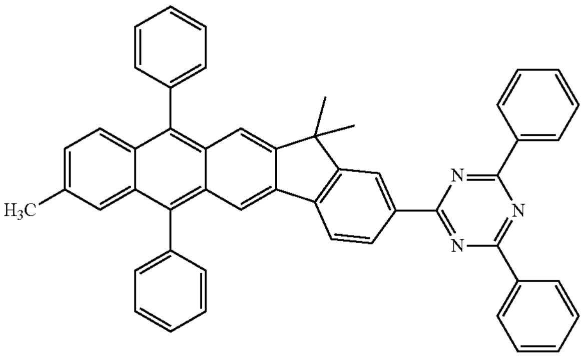
Compound 8
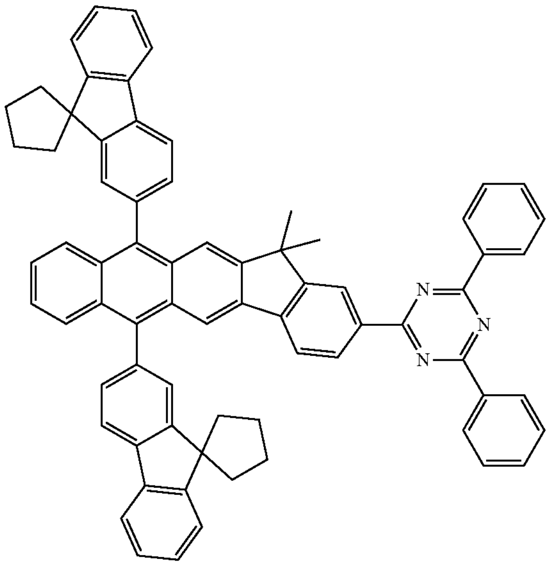

-continued
Compound 9
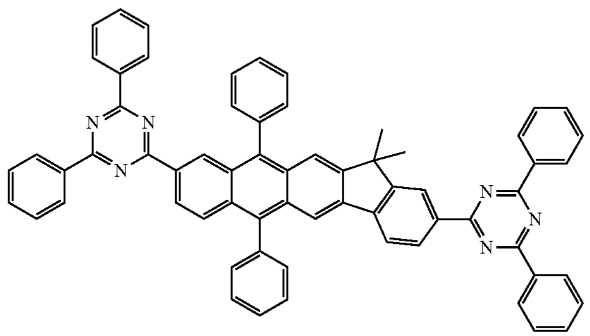
Compound 10
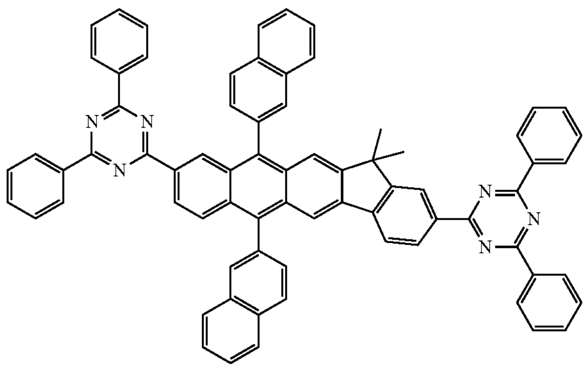
Compound 11
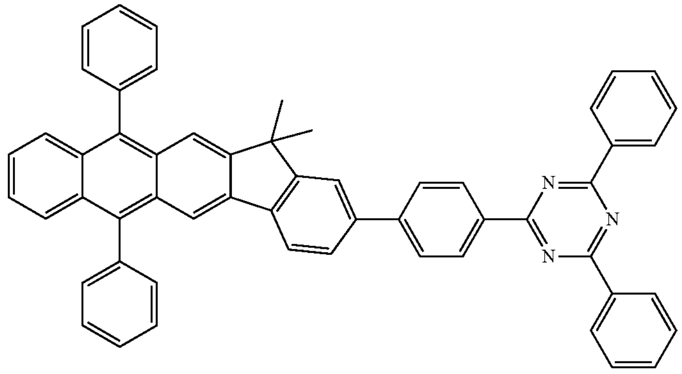
Compound 12
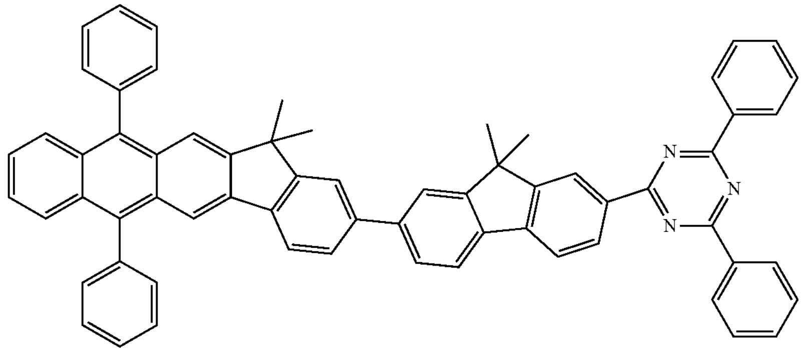
Compound 13
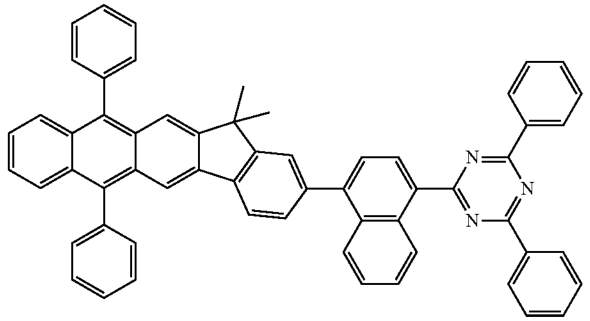
Compound 14
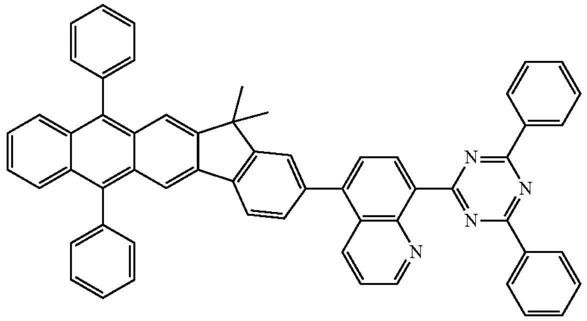

-continued
Compound 15
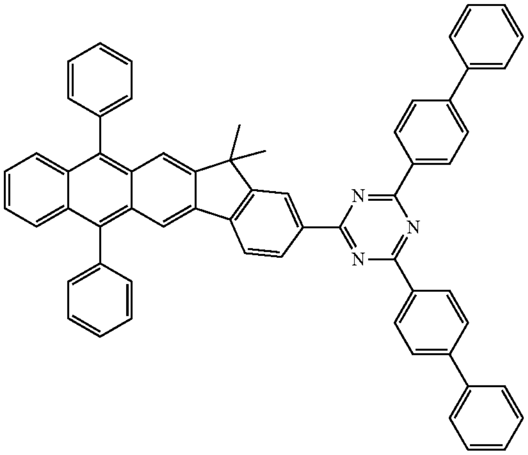
Compound 16
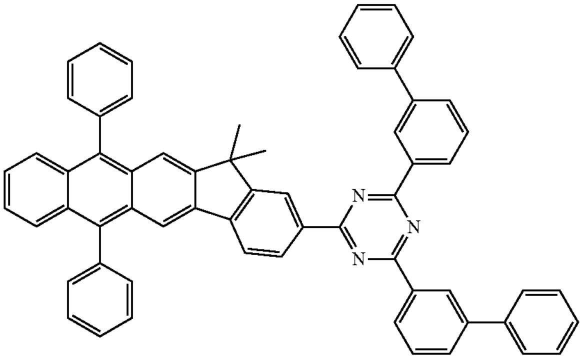
Compound 17
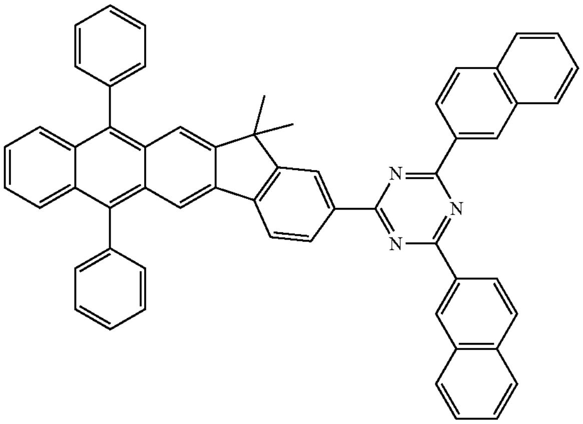
Compound 18
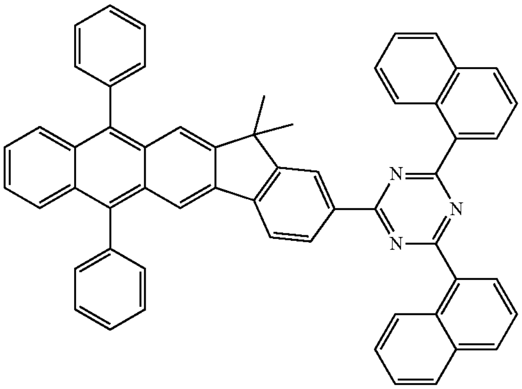
Compound 19
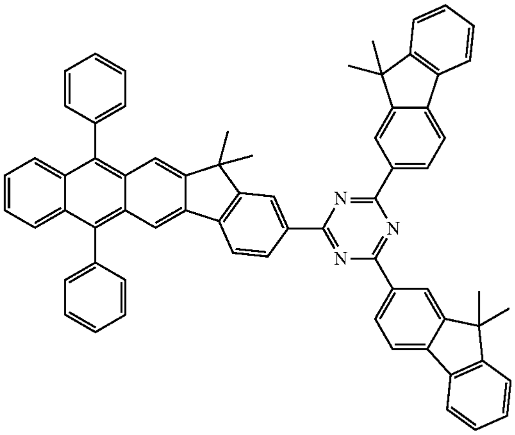
Compound 20
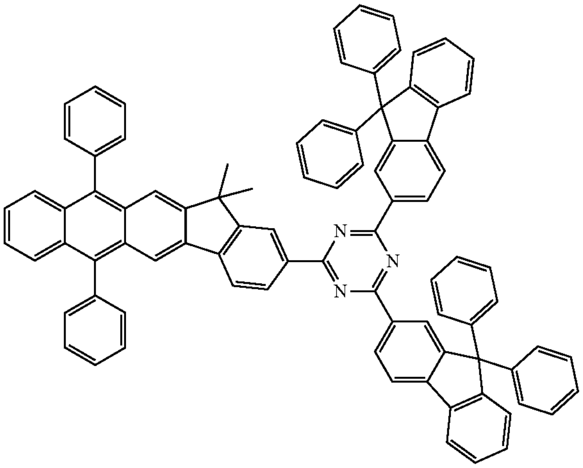

-continued
Compound 21
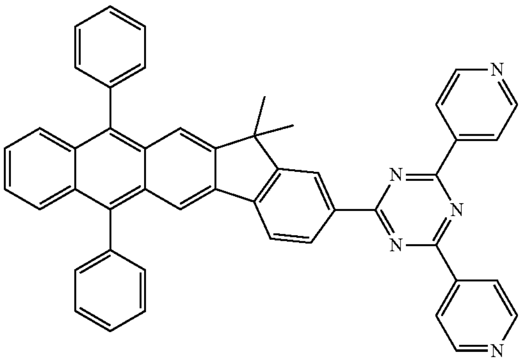
Compound 22
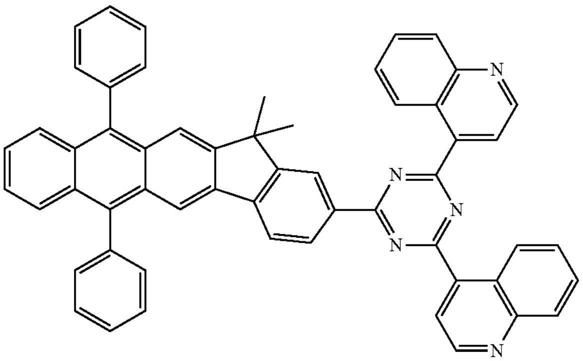
Compound 23
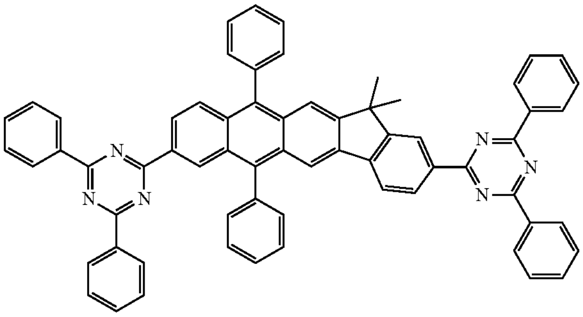
Compound 24
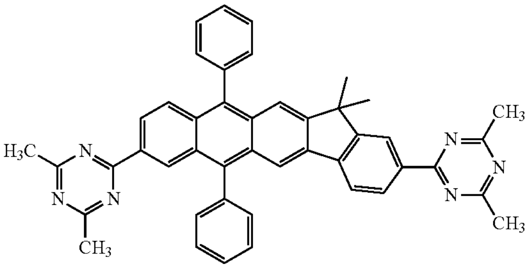
Compound 25
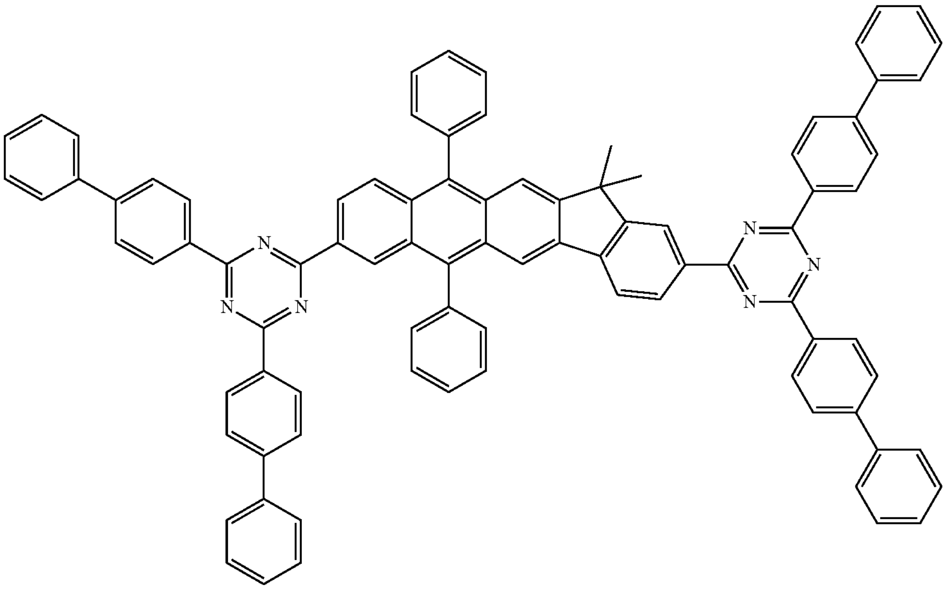

-continued
Compound 26
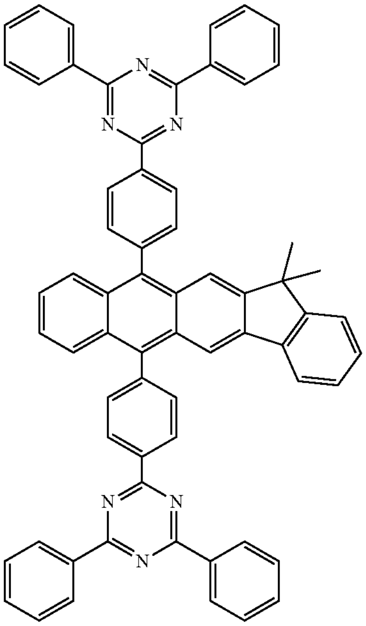
Compound 27
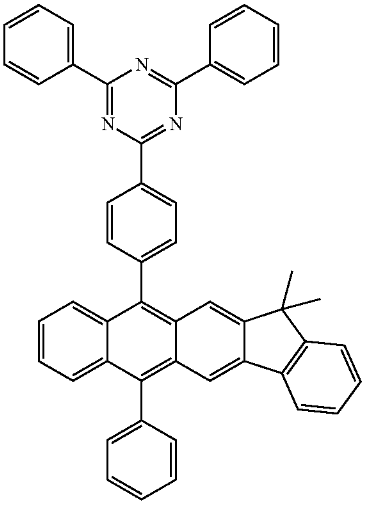
Compound 28
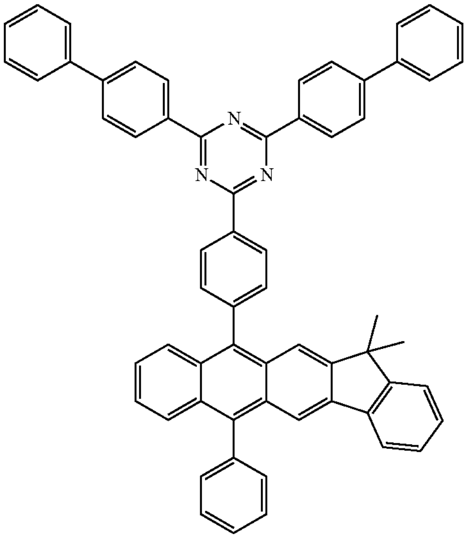
Compound 29
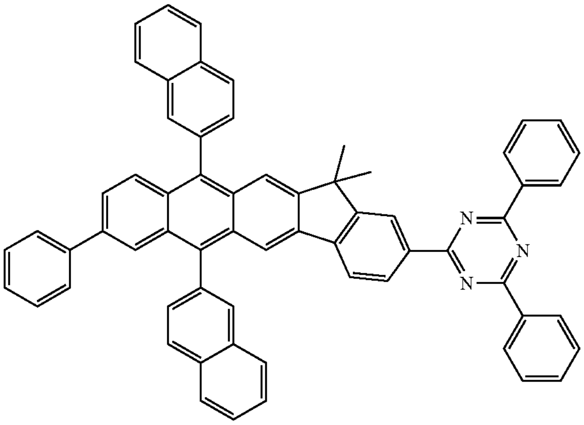

-continued
Compound 30
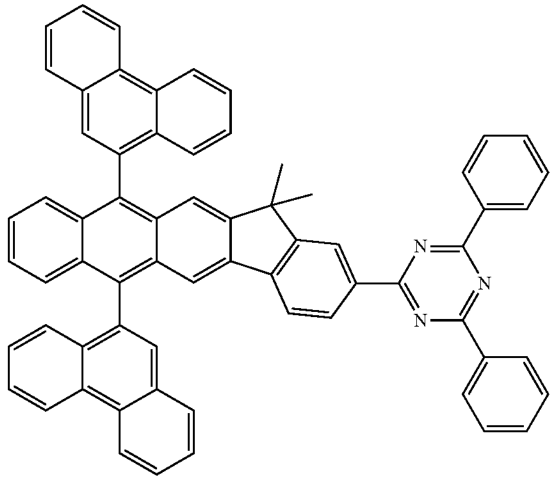
Compound 31
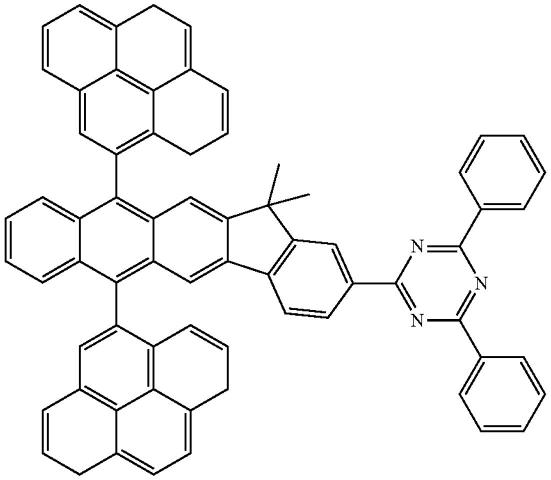
Compound 32
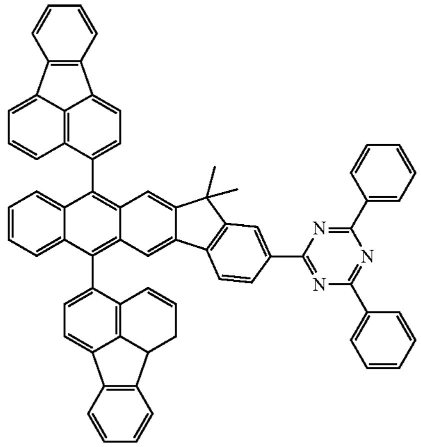
Compound 33
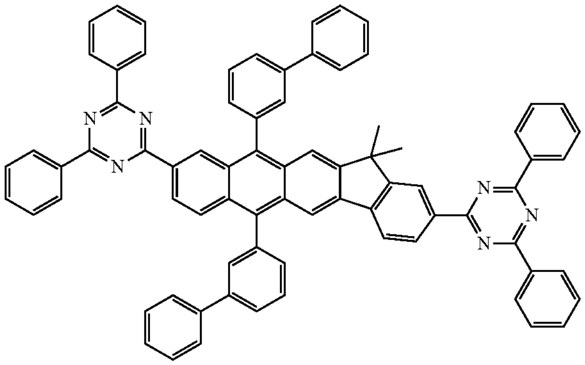
Compound 34
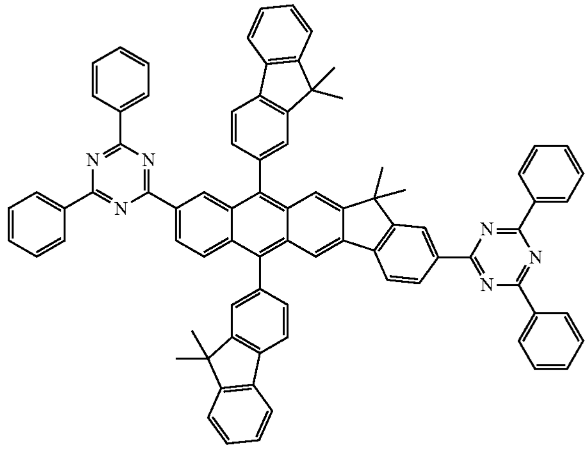
Compound 35
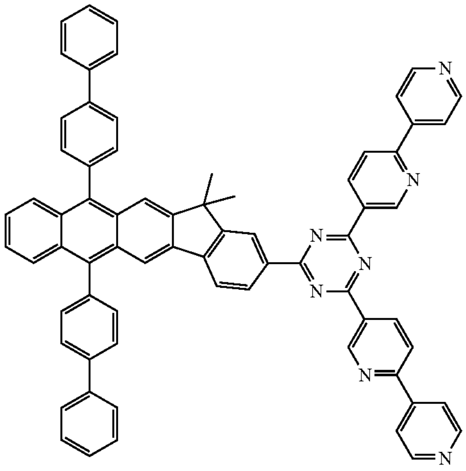

-continued
Compound 36
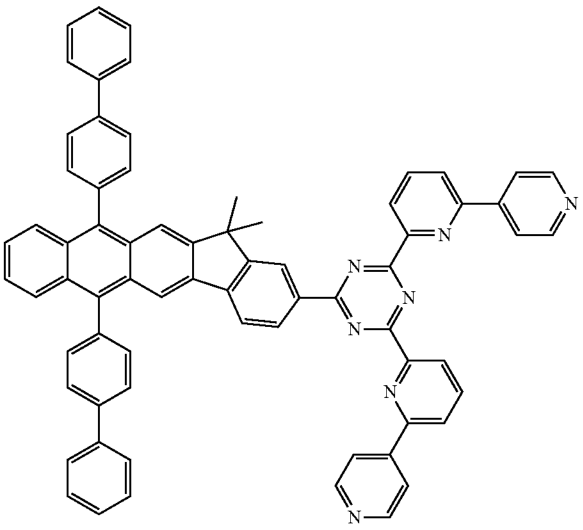
Compound 37
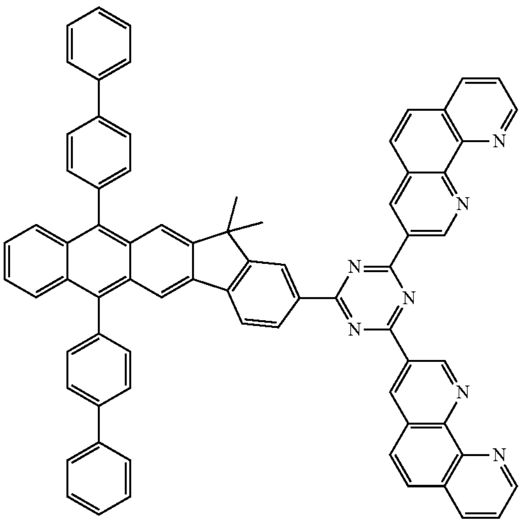
Compound 38
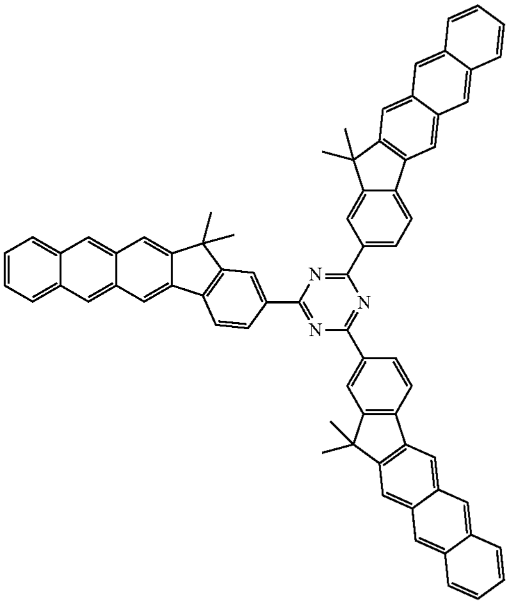
Compound 39
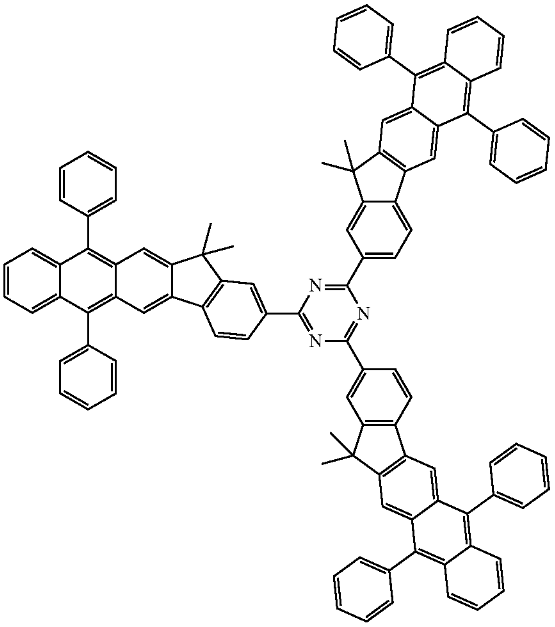

-continued

Compound 40

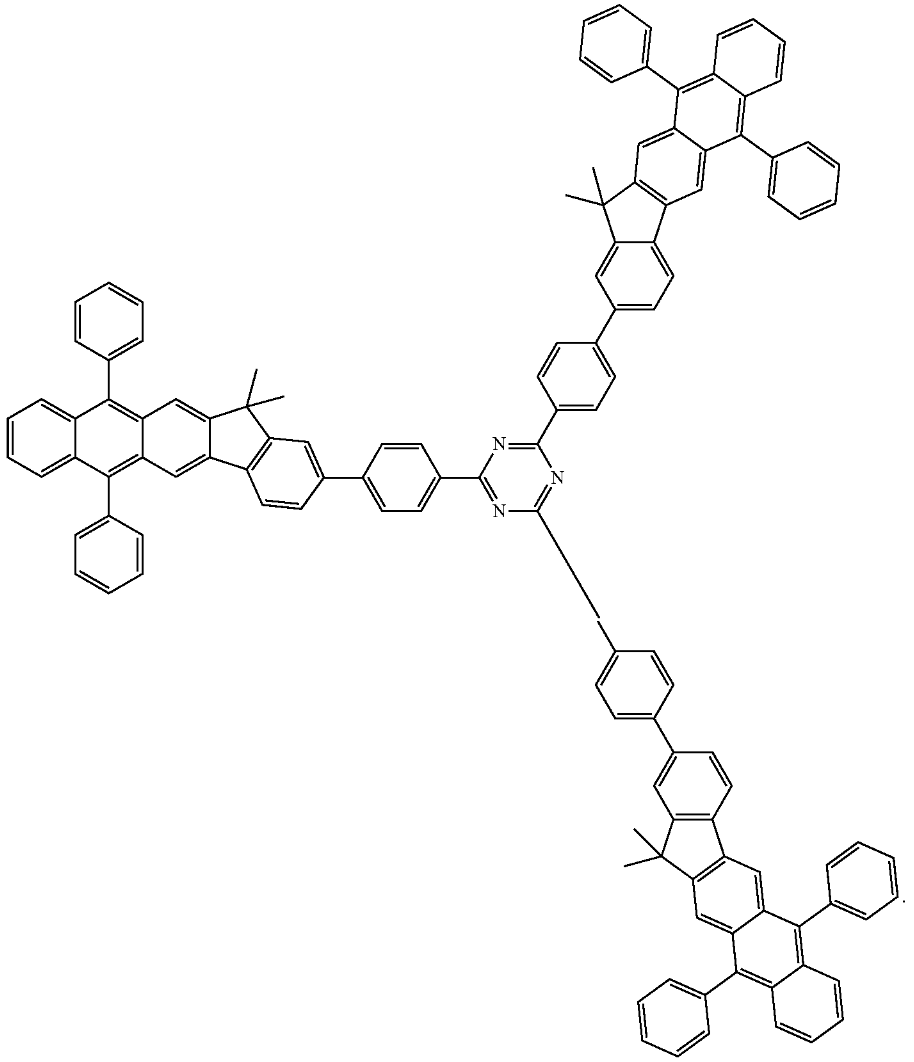

14. An organic light-emitting device comprising:

a first electrode;

a second electrode facing the first electrode; and an organic light-emitting device comprising at least one organic layer between the first electrode and the second electrode, wherein the at least one organic layer comprises the condensed-cyclic compound of claim 1.

15. The organic light-emitting device of claim 14, wherein the organic layer comprises an electron injection layer, an electron transport layer, or a single layer having both electron injection and electron transport functions.

16. The organic light-emitting device of claim 14, wherein the at least one organic layer is an emission layer.

17. The organic light-emitting device of claim 14, wherein the at least one organic layer is an emission layer, the condensed-cyclic compound is a fluorescent host or a phosphorescent host, and the emission layer further comprises a fluorescent dopant or a phosphorescent dopant.

18. The organic light-emitting device of claim 14, further comprising at least one layer selected from the group consisting of a hole injection layer, a hole transport layer, an electron blocking layer, a hole blocking layer, an electron transport layer, and an electron injection layer between the first electrode and the second electrode.

19. The organic light-emitting device of claim 14, wherein the organic light-emitting device has a first electrode/hole injection layer/emission layer/electron transport layer/electron injection layer/second electrode structure, a first electrode/hole injection layer/hole transport layer/emission layer/electron transport layer/electron injection layer/second electrode structure, or a first electrode/hole injection layer/hole transport layer/emission layer/hole blocking layer/electron transport layer/electron injection layer/second electrode structure.

20. A flat panel display apparatus comprising:

a transistor comprising a source electrode, a drain electrode, a gate, and an active layer, and the organic light-emitting device of claim 14, wherein the first electrode of the organic light-emitting device is electrically connected to the source electrode or the drain electrode of the transistor.

* * * * *